(12) United States Patent
Ghandi

(10) Patent No.: US 8,791,188 B2
(45) Date of Patent: Jul. 29, 2014

(54) PROCESS FOR THE PRODUCTION OF POLYSTYRENE IN AN IONIC LIQUID AND NOVEL POLYMERS THEREOF

(75) Inventor: Khashayar Ghandi, Sackville (CA)

(73) Assignee: ChemGreen Innovations Inc., Sackville, New Brunswick (CA)

( * ) Notice: Subject to any disclaimer, the term of this patent is extended or adjusted under 35 U.S.C. 154(b) by 154 days.

(21) Appl. No.: 13/259,581

(22) PCT Filed: Mar. 24, 2010

(86) PCT No.: PCT/CA2010/000436
§ 371 (c)(1),
(2), (4) Date: Oct. 27, 2011

(87) PCT Pub. No.: WO2010/108271
PCT Pub. Date: Sep. 30, 2010

(65) Prior Publication Data
US 2012/0049101 A1    Mar. 1, 2012

Related U.S. Application Data

(60) Provisional application No. 61/162,828, filed on Mar. 24, 2009.

(51) Int. Cl.
*C08K 3/32* (2006.01)
*H01F 1/26* (2006.01)

(52) U.S. Cl.
USPC .................................. 524/414; 252/62.54

(58) Field of Classification Search
USPC .............................................. 524/414
See application file for complete search history.

(56) References Cited

U.S. PATENT DOCUMENTS

| | | | |
|---|---|---|---|
| 5,304,615 A | 4/1994 | Ambler et al. | |
| 5,731,101 A | 3/1998 | Sherif et al. | |
| 6,924,341 B2 | 8/2005 | Mays et al. | |
| 7,148,302 B2 | 12/2006 | Lipian | |
| 7,199,074 B2 | 4/2007 | Goodall et al. | |
| 7,438,832 B2 | 10/2008 | Majumdar et al. | |
| 7,625,941 B2 | 12/2009 | Harmer et al. | |
| 7,626,748 B2 | 12/2009 | Radmard et al. | |
| 7,651,970 B2 | 1/2010 | Elomari et al. | |
| 2002/0010291 A1 | 1/2002 | Murphy | |
| 2004/0050207 A1* | 3/2004 | Wooldridge et al. | 75/362 |
| 2005/0014644 A1 | 1/2005 | Ray et al. | |
| 2009/0030122 A1* | 1/2009 | Matsuda et al. | 524/99 |

OTHER PUBLICATIONS

Myasoedova et al., Analytical Sciences, vol. 24, pp. 1351-1353, Oct. 2008.*
Zhang et al., American Chemical society, ACS Sympoisium Series, 913, pp. 1-15, Washington, Dc, Jul. 2005.*
J. Ryan et al., First Nitroxide-Mediated Controlled/Living Free Radical Polymerization in an Ionic Liquid. Macromol. Rapid Commun, 2004, 25, 930.
R. Sheldon, Catalytic reactions in ionic liquids. Chem. Commun. 2001, 23:2399-407.
K. Hong, et al., Conventional free radical polymerization in room temperature ionic liquids: a green approach to commodity polymers with practical advantages. Chem. Commun. 2002, 13:1368-9.
S. Harrison. Pulsed Laser Polymerization in an Ionic Liquid: Strong Solvent Effects on Propagation and Termination of Methyl Methacrylate. Macromolecules 2003, 36, 5072.
A. J. Carmichael, et al. Copper(I) Mediated Living Radical Polymerisation in an Ionic Liquid. Chem. Commun. 2000, 1237-1238.
T. Biedron, P. Kubisa. Atom-Transfer Radical Polymerization of Acrylates in an Ionic Liquid. Macromol. Rapid Commun. 2001, 22, 1237-1242.
T. Sarbu, K. Matyjaszewski. ATRP of Methyl Metharylate in the Presence of Ionic Liquids with Ferrous and Cuprous Anions. Macromol. Chem. Phys. 2001, 202, 3379.
P. Cormier, et al. Free Radical Formation in Supercritical CO(2), Using Muonium as Probe and Implication for H Atom Reaction with Ethene. J. Phys. Chem. A, 2008, 112, 4593.
P. Cormier, et al. Hyperfine Interactions of Muoniated Ethyl Radical in Supercritical. Physica B, 2009, 404, 930.
K. Ghandi, et al., Laser-muon spin spectroscopy in liquids—a technique to study the excited state chemistry of transients. Phys. Chem. Chem. Phys., 2007, 9:353-359.
J. M. Lauzon, et al., Generation and detection of the cyclohexadienyl radical in phosphonium ionic liquids. Phys. Chem. Chem. Phys., 2008, 10(39):5957-5962.
B. A. Taylor, et al. Investigating the Solvent and Temperature Effects on the Cyclohexadienyl Radical in an Ionic Liquid. Physica B, 2009, 404, 936.
N. Ishihara et al. Crystalline Syndiotactic Polystyrene. Macromolecules, 1986, 19, 2464-2465.
P. Snedden et al. Cross-Linked Polymer-Ionic Liquid Composite Materials. Macromolecules 2003, 36:4549-4556.
R. Vijayaraghavan et al. Anionic Polymerization of Styrene in Ionic Liquids. European Polymer Journal, 2008, 44:1758-1762.
H. Zhang et al. Free Radical Polymerization of Styrene and Methyl Methacrylate in Various Room Temperature Ionic Liquids. American Chemical Society. 2005, Chapter 1, 1-11.
H. Zhang et al. Ionic Liquids, Polymerization in. Encyclopedia of Polymer Sciences and Technology. 2005, 1-15.
T. Sarbu and K. Matyjaszewski. ATRP of Methyl Methacrylate in the Presence of Ionic Liquids with Ferrous and Cuprous Anions. Macromol. Chem. Phys. 202:3379-3391, 2001.
M. Lee et al. Structure and Properties of N,N-Alkylene Bis(N'-Alkylimidazolium) Salts. J. Phys. Chem. B. 2010, 114:7312-7319.
E. C. Buruiana et al. Synthesis and Characterization of Liquid Crystalline Alkylammonium Polyacrylates. Macromol. Rapid Commun. 2002, 23:130-134.

(Continued)

*Primary Examiner* — Hui Chin
(74) *Attorney, Agent, or Firm* — Bereskin & Parr LLP/S.E.N.C.R.L., s.r.l.; Michael Fenwick

(57) ABSTRACT

The present disclosure relates a polymer composite comprising a polystyrene or a polystyrene derivative comprising styrene or styrene derivative monomer units in which at least about 1% (mole fraction) of a phosphonium ion salt ionic liquid is incorporated into the structure of the polystyrene or polystyrene derivative, and processes for the production thereof.

20 Claims, 29 Drawing Sheets

(56) References Cited

OTHER PUBLICATIONS

H. Chen et al. ARGET ATRP of Acrylonitrile with Iionic Liquid as Reaction Media and 1,1,4,7,7-pentamethyl-diethyllenetriamine as Both Ligand and Reducing Agent in the Presence of Air. Polym. Adv. Technol. 2011, 22:1513-1517.

H. Chen et al., ARGET ATRP of Acrylonitrile with Ionic Liquid As Reaction Medium and FeBr(3)/Isophthalic Acid as Catalyst System. Journal of Applied Polymer Science, 122:3298-3302, 2011.

H. Chen et al. Atom Transfer Radical Polymerization Using Activators Regenerated by Electron Transfer of Acrylonitrile in 1-(1-Ethoxycarbonylethyl)-3- methylimidazolium Henxafluorophospate. Journal of Polymer Science: Part A: Polymer Chemistry, 49:-1046-1049, 2011.

N. Winterton. Solubilization of Polymers by Ionic Liquids. J. Mater. Chem. 2006, 16:4281-4293.

T. Biedron et al. Cationic Polymerization of 3-Ethyl-3-Hydroxymethyloxetane in an Ionic Liquid. Macromol. Rapid Commun. 2004, 25:878-881.

E. Rafiemanzelat and Elahe Abdollahi. Rapid Synthesis of New Block Copolyurethanes Derived from L-Leucine Cyclodipeptide in Reusable Molten Ammonium Salts: Novel and Efficient Green Media for the Synthesis of New Hydrolysable and Biodegradable Copolyurethanes. Springer. 2011.

M. D. Green and T.E. Long. Designing Imidazole-Based Ionic Liquids and Ionic Liquid Monomers for Emerging Technologies. Journal of Macromolecular Science, Part C: Polymer Reviews, 49:291-314, 2009.

M. Lee et al. Imidazolium Polyesters: Structure-Property Relationships in Thermal Behavior, Ionic Conductivity, and Morphology. Adv. Funct. Mater. 2011, 21:708-717.

R. L. Weber et al. Thermal and Ion Transport Properties of Hydrophilic and Hydrophobic Polymerized Styrenic Imidazolium Ionic Liquids. Journal of Polymer Science. Part B: Polymer Physics, 2011, 49:1287-1296.

Y. Ye and Yossef A. Elabd. Relative Chemical Stability of Imidazolium-Based Alkaline Anion Exchange Polymerized Ionic Liquids. Macomolecules, 2011, 44:8494-8503.

A.S. S Amarasekara et al. Synthesis and Characterization of Branched Polymeric Iionic Liquids with Imidazolium Chloride Segments. Polym. Bull. 2011.

P. Izak et al. Increased Productivity of Clostridium Acetobutylicum Fermentation of Acetone, Butanol, and Ethanl by Pervaporation of Acetone, Butanol, and Ethanol by Pervaporation Through Supported Ionic Liquid Membrane. Appl. Microbiol. Biotechnol. 2008, 78:597-602.

Y-H Shih et al. A Rapid Synthetic Method for Organic Polymer-Based Monoliths in a Room Temperature Ionic Liquid Medium Via Microwave-Assisted Vinylization and Polymerization. Green Chem., 2011, 13:296-299.

S. Brusseau et al. Nitroxide-Mediated Controlled/Living Raidcal Coplymerization of Methyl Methacrylate with a Low Amount of Styrene in Ionic Liquid. Macromolecules, 2011, 44:215-220.

S.A. Chesnokov et al. Photopolymerization of Poly(ethylene glycol) Dimethacrylates: The Influence of Ionic Liquids on the Formulation and the Properties of the Resultant Polymer Materials. Journal of Polymer Science: Part A: Polymer Chemistry, 48:2388-2409, 2010.

J-I Kadokawa et al. Ring-Opening Polymerization of Ethylene Carbonate Catalyzed with Ionic Liquids: Imidazolium Chloroaluminate and Chlorostannate Melts. Macromol. Rapid. Commun. 2002, 23:757-760.

X. Li et al. An In-Situ X-Ray Scattering Study During Uniaxial Stretching of Ionic Liquid/Ultra-High Molecular Weight Polyethylene Blends. Polymer, 52:4610-4618, 2011.

O. Jazkewitsch and Helmut Ritter. Polymerizable Ionic Liquid Crystals. Macromol. Rapid Commun. 2009, 30:1554-1558.

J- Y. Lee Radiation-Grafted Fluoropolymers Soaked with Imidazolum-Based Ionic Liquids for High-Performance Ionic Polymer-Metal Composite Actuators. Macromol. Rapid Commun. 2010, 31:1897-1902.

G. Cui et al. Organostibine-Mediated Controlled/Living Radical Polymerization of Methyl Methacrylate and Styrene in Ionic Liquid. Macromol. Chem. Phys. 2010, 211:1222-1228.

V. Jovanovski et al. Tuning the Properties of Functional Pyrrolidinium Polymers by (Co)polymerization of Diallyldimethylammonium Ionic Liquids. Macormol. Rapid Commun. 2010, 31:1646-1651.

G. Wu et al. Effects of Ionic Liquid [Me(3)NC(2)H(4)OH]+[ZnCl(3)]- on Gamma-Radiation Polymerization of Methyl Methacrylate in Ethanol ad N,N-Dimethylformamide. Macromol. Rapid Commun. 2005, 26:57-61.

G. Johnston-Hall et al. RAFT-Mediated Polymerization of Styrene in Readily Biodegradable Ionic Liquids. Macromolecules, 2009, 42:1604-1609.

W.A. Yee et al. Supercritical Carbon Dioxide-Treated Electrospun Poly(vinylidene fluoride) Nanofibrous Membranes: Morphology, Structures and Properties as an Ionic-Liquid Host. Macromol. Rapid Commun. 2010, 31:1779-1784.

H. Zhang et al. Synthesis of Block Copolymers of Styrene and Methyl Methacrylate by Conventional Free Radical Polymerization in Room Temperature Ionic Liquids. Macromolecules. 35:5738-5741, 2002.

V. Strehmel. Ionische Flussigkeiten in der Polymersynthese. Chemie Ingenieur Technik, 83:(9), 1443-1453, 2011.

\* cited by examiner 200.0   100.0   0   -100.0   -200.0

PROCESS FOR THE PRODUCTION OF POLYSTYRENE IN AN IONIC LIQUID AND NOVEL POLYMERS THEREOF

PRIORITY INFORMATION

This application is a national phase entry of PCT/CA2010/000436, filed Mar. 24, 2010, which claims priority from U.S. Provisional patent application Ser. No. 61/162,828 filed Mar. 24, 2009, each of these applications being incorporated herein in their entirety by reference.

This application claims the benefit of 35 USC 119 based on the priority of U.S. Provisional Patent Application No. 61/162,828, filed Mar. 24, 2009, this application being incorporated herein in its entirety by reference.

FIELD OF THE DISCLOSURE

The present disclosure relates to a polymer composite comprising a polystyrene or a polystyrene derivative comprising styrene monomer units in which at least about 1% (mole fraction) of a phosphonium ion salt ionic liquid is incorporated into the structure of the polystyrene or polystyrene derivative, and processes for the production thereof.

BACKGROUND OF THE DISCLOSURE

Ionic liquids are relatively new "green" solvents and generally possess high thermal stabilities and low vapor pressures. Further, ionic liquids are also slightly miscible in water and have a wide liquid range as a result of the wide range of cations and anions that can be combined to form the ionic liquid. Generally, ionic liquids possess a bulky organic cation and an associated anion, as shown for example, in Scheme 1.

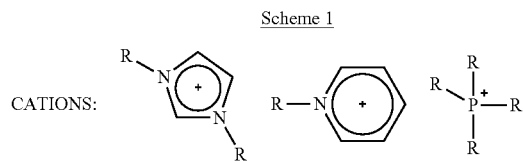

Recently, imidazolium based ionic liquids were used to replace conventional organic solvents in free radical polymerizations.[1-7] In addition, research has been conducted at the interface of the three different fields of free radical chemistry [8, 9], photochemical reactions [10] and ionic liquids [11, 12].

The styrene monomer (SM) is the immediate precursor for all forms of polystyrene (PS). The polymerization reaction is represented in Scheme 2, which is typically a free radical propagation.

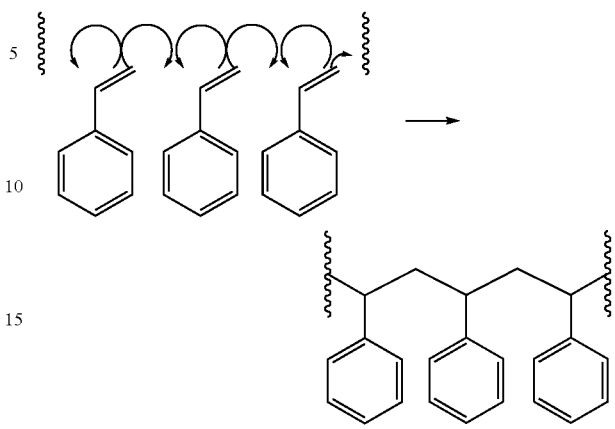

Polystyrene is a common polymer found in a wide range of products, from disposable cutlery to Styrofoam-brand packing material. The polystyrene industry is worth more than $28 billion in the U.S. alone. Generally, this process is carried out on an industrial scale using volatile organic solvents, which are harmful to the environment.

SUMMARY OF THE DISCLOSURE

The production of polystyrene has been successfully performed in an ionic liquid with conversion yields of the styrene monomer units to polystyrene of up to, and including, 100% efficiency. Further, the polymerization of polystyrene from the styrene monomer units is performed at pressures at or near atmospheric pressure (1 atm). The disclosure also relates to new polystyrene and polystyrene derivative composites produced from styrene monomer units and ionic liquids.

Accordingly, the present disclosure includes a polymer composite comprising a polystyrene or a polystyrene derivative in which at least about 1%, about 2%, about 5%, about 10%, about 15%, about 20% or about 25% (mole fraction) of a phosphonium ion salt ionic liquid is incorporated into the structure of the polystyrene or polystyrene derivative.

In another embodiment, the polystyrene or a polystyrene derivative is prepared from at least one styrene monomer unit that is a compound of the formula (I)

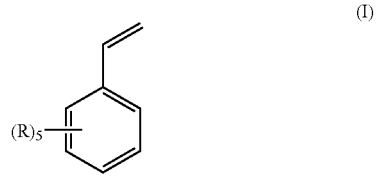

wherein
each R is simultaneously or independently H, halo or $C_{1-4}$alkyl, the latter group being optionally substituted by halo, $C_{1-2}$alkyl or fluoro-substituted $C_{1-2}$alkyl. In a further embodiment, each R is simultaneously or independently H, methyl or ethyl. In another embodiment, each R is H.

In another embodiment, the phosphonium ion salt ionic liquid has the structure:

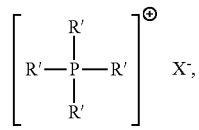

wherein each R' is independently or simultaneously $C_{1-20}$alkyl and X is any suitable anionic ligand. In another embodiment, each R' is independently or simultaneously methyl, ethyl, propyl, butyl, isobutyl, pentyl, hexyl, heptyl, octyl, nonyl, decyl, undecyl, dodecyl, tridecyl, tetradecyl, pentadecyl or hexadecyl.

In another embodiment, X is chloride, bromide, decanoate, (bis 2,4,4-trimethylpentyl)phosphinate, dicyanamide, tosylate, methylsulfate, bistriflamide, hexafluorophosphate, tetrafluoroborate, diethylphosphate or dedecylsulfonate.

In another embodiment, the phosphonium ion salt ionic liquid is tetradecyl(trihexyl)phosphonium chloride, tetradecyl(trihexyl)phosphonium bromide, tetradecyl(trihexyl) phosphonium decanoate, tetradecyl(trihexyl)phosphonium (bis 2,4,4-trimethylpentyl)phosphinate, tetradecyl(trihexyl) phosphonium dicyanamide, triisobutyl(methyl) phosphonium tosylate, tributyl(methyl)phosphonium methylsulfate, tetradecyl(trihexyl)phosphonium bistriflamide, tetradecyl(trihexyl)phosphonium hexafluorophosphate, tetradecyl(trihexyl)phosphonium tetrafluoroborate, tributyl(hexadecyl)phosphonium bromide, tetrabutylphosphonium bromide, tetrabutylphosphonium chloride, tetraoctylphosphonium bromide, tetradecyl(tributyl)phosphonium chloride, ethyltri(butyl)phosphonium diethylphosphate, tetradecyl(tributyl)phosphonium dodecylsulfonate or tetradecyl (trihexyl)phosphonium dodecylsulfonate.

In a further embodiment, the phosphonium ion salt ionic liquid is selected from

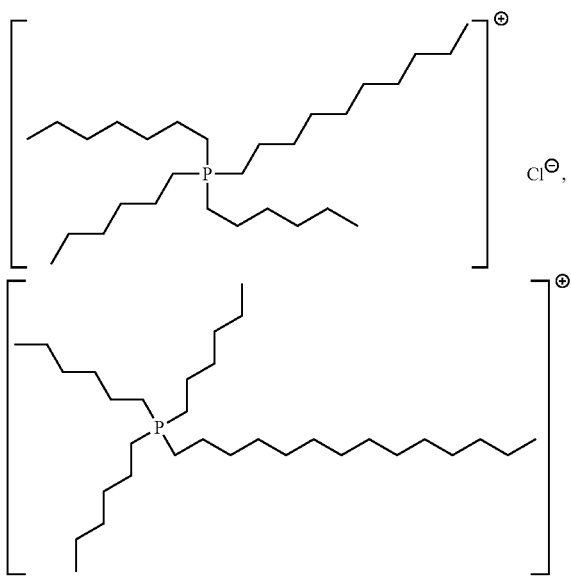

-continued

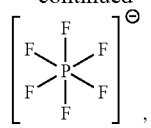

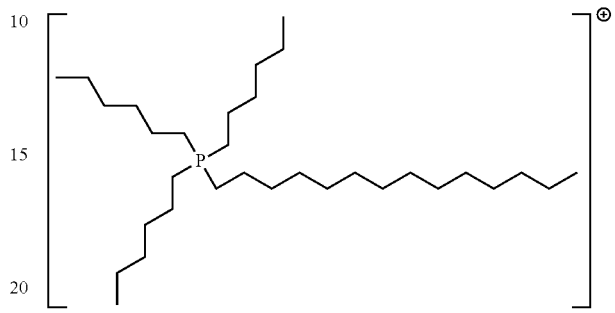

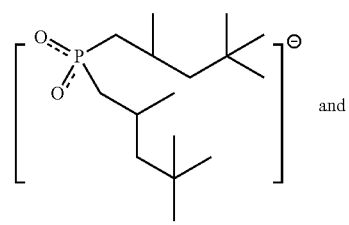

and

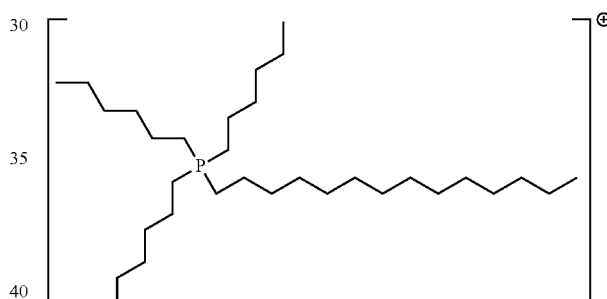

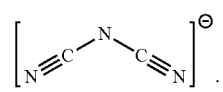

In another embodiment, the polymer composite comprising a polystyrene or a polystyrene derivative and the phosphonium ion salt, further comprises a metal dopant. In another embodiment, the metal dopant is a magnetic metal, such as copper, iron. In another embodiment, the metal dopant comprises gold nanoparticles.

In another embodiment, the present disclosure also includes a process for the production of polystyrene or a polystyrene derivative, comprising polymerizing styrene or styrene derivative monomer units in a phosphonium ion salt ionic liquid in the presence of a free radical initiator at a pressure of about 0.8 to about 1.2 atmospheres, under conditions for the polymerization of the styrene monomer units, in which the phosphonium ion salt is incorporated into the polystyrene or a polystyrene derivative.

In another embodiment, at feast about 1%, about 2%, about 5%, about 10%, about 15%, about 20% or about 25% (mole fraction) of a phosphonium ion salt ionic liquid is incorporated into the structure of the polystyrene or polystyrene derivative.

In another embodiment, the phosphonium ion salt ionic liquid has the structure:

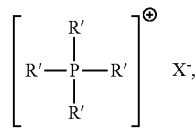

wherein
each R' is independently or simultaneously $C_{1-20}$alkyl and X is any suitable anionic ligand. In another embodiment, each R' is independently or simultaneously methyl, ethyl, propyl, butyl, isobutyl, pentyl, hexyl, heptyl, octyl, nonyl, decyl, undecyl, dodecyl, tridecyl, tetradecyl, pentadecyl or hexadecyl.

In another embodiment, X is chloride, bromide, decanoate, (bis 2,4,4-trimethylpentyl)phosphinate, dicyanamide, tosylate, methylsulfate, bistriflamide, hexafluorophosphate, tetrafluoroborate, diethylphosphate or dedecylsulfonate.

In another embodiment, the phosphonium ion salt ionic liquid is tetradecyl(trihexyl)phosphonium chloride, tetradecyl(trihexyl)phosphonium bromide, tetradecyl(trihexyl)phosphonium decanoate, tetradecyl(trihexyl)phosphonium (bis 2,4,4-trimethylpentyl)phosphinate, tetradecyl(trihexyl)phosphonium dicyanamide, triisobutyl(methyl)phosphonium tosylate, tributyl(methyl)phosphonium methylsulfate, tetradecyl(trihexyl)phosphonium bistriflamide, tetradecyl(trihexyl)phosphonium hexafluorophosphate, tetradecyl(trihexyl)phosphonium tetrafluoroborate, tributyl(hexadecyl)phosphonium bromide, tetrabutylphosphonium bromide, tetrabutylphosphonium chloride, tetraoctylphosphonium bromide, tetradecyl(tributyl)phosphonium chloride, ethyltri(butyl)phosphonium diethylphosphate, tetradecyl(tributyl)phosphonium dodecylsulfonate or tetradecyl(trihexyl)phosphonium dodecylsulfonate.

In another embodiment, the phosphonium ion salt is selected from

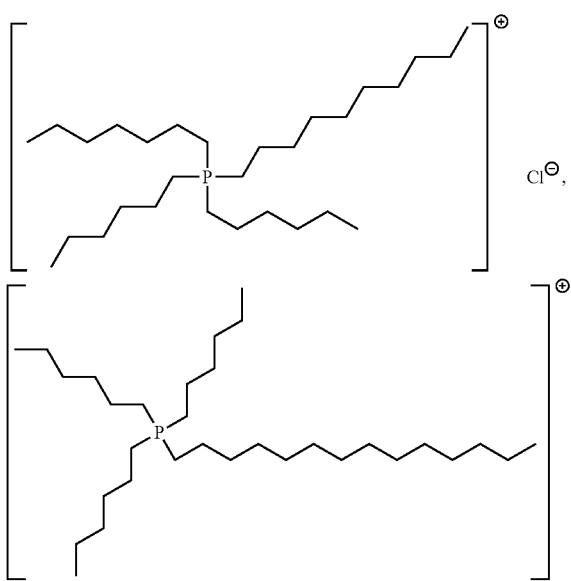

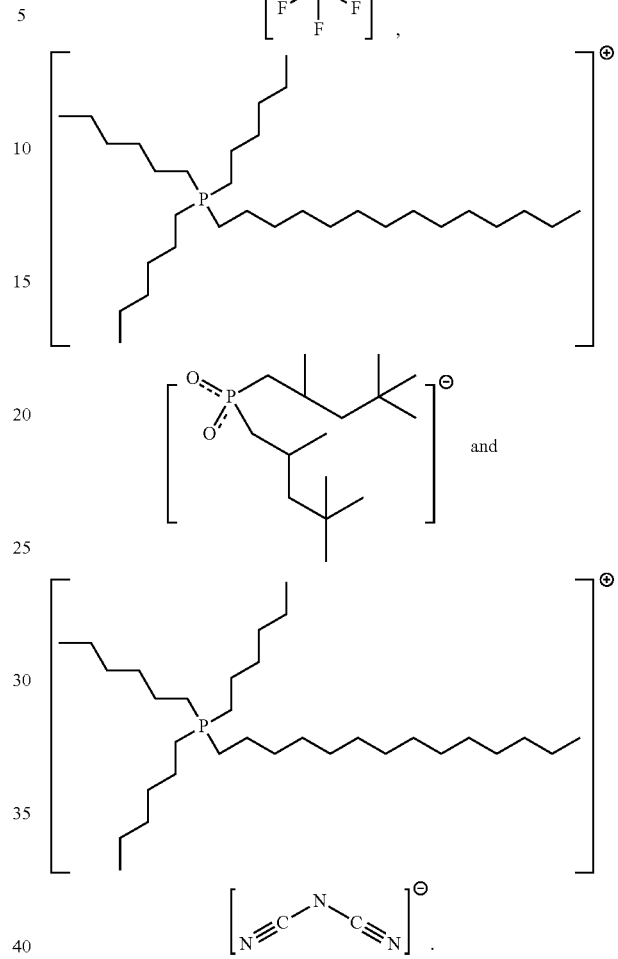

In an embodiment of the disclosure, the styrene or styrene derivative monomer unit is a compound of the formula (I)

(I)

wherein
each R is simultaneously or independently H, halo or $C_{1-4}$alkyl, the latter group being optionally substituted by halo, $C_{1-2}$alkyl or fluoro-substituted $C_{1-2}$alkyl. In a further embodiment, each R is simultaneously or independently H, methyl or ethyl. In another embodiment, each R is H.

In another embodiment of the present disclosure, the free radical initiator is selected from benzoyl peroxide, hydrogen peroxide and azobisisobutyronitrile (AIBN). In another embodiment, the free radical initiator is present in an amount of about 0.05% to about 3% (v/v). In a further embodiment, the free radical initiator is present in an amount of about 0.1% to about 2% (v/v).

In a further embodiment of the present disclosure, the polymerization is performed at a pressure of about 0.9 to about 1.1 atmospheres. In another embodiment, the polymerization is performed at a pressure of about 1.0 atmosphere. In another embodiment, the polymerization is performed at about atmospheric pressure.

In an embodiment, the conditions for the polymerization of the styrene or styrene derivative monomer units comprise a temperature of about 10° C. to about 100° C. In a further embodiment, the conditions for the polymerization of the styrene or styrene derivative monomer units comprise a temperature of about 25° C. to about 80° C. In another embodiment, the conditions for the polymerization of the styrene or styrene derivative monomer units comprise a temperature of about 25° C.

In a further embodiment of the present disclosure, the conditions for the polymerization of the styrene or styrene derivative monomer units comprise a mole fraction ratio of the styrene monomer units to the phosphonium ion salt ionic liquid of about 0.10:1.0 to about 2.0:1.0 (styrene monomer units:ionic liquid). In a further embodiment of the present disclosure, the conditions for the polymerization of the styrene or styrene derivative monomer units comprise a mole fraction ratio of the styrene or styrene derivative monomer units to the phosphonium ion salt ionic liquid of about 0.10:1.0 to about 1.0:1.0 (styrene or styrene derivative monomer units:ionic liquid). In another embodiment, the conditions for the polymerization of the styrene or styrene derivative monomer units comprise a mole fraction ratio of the styrene or styrene derivative monomer units to the phosphonium ion salt ionic liquid of about 0.11:1.0 to about 0.33:1.0 (styrene or styrene derivative monomer units:ionic liquid).

In an embodiment of the disclosure, the conditions for the polymerization of the styrene or styrene derivative monomer units comprise microwave energy.

In another embodiment, the conditions for the polymerization of the styrene or styrene derivative monomer units comprise ultraviolet light.

In another embodiment, the polystyrene or a polystyrene derivative precipitates from the phosphonium ion salt ionic liquid leaving unreacted styrene or styrene derivative monomer units and ionic liquid, wherein the unreacted styrene or styrene derivative monomer units and ionic liquid are further reacted using the process of the disclosure. In another embodiment, the total yield of the polystyrene or polystyrene derivative is at least 90%, at least about 95%, at least about 98%, at least about 99%, at least about 99.9%, or 100%. In the case of 100% yield, there is no need for separation of the starting materials, as all of the reactants are consumed.

In another embodiment, the present disclosure also includes a process for the production of polystyrene or a polystyrene derivative, comprising polymerizing styrene or styrene derivative monomer units in a phosphonium ion salt ionic liquid in the presence of a free radical initiator, under conditions for the polymerization of the styrene or styrene derivative monomer units, in which the phosphonium ion salt is incorporated into the polystyrene or the polystyrene derivative.

In another embodiment, at least about 1%, about 2%, about 5%, about 10%, about 15%, about 20% or about 25% (mole fraction) of a phosphonium ion salt ionic liquid is incorporated into the structure of the polystyrene or polystyrene derivative.

In another embodiment, the phosphonium ion salt has the structure:

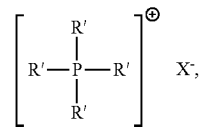

wherein
each R' is independently or simultaneously $C_{1-20}$alkyl and X is any suitable anionic ligand. In another embodiment, each R' is independently or simultaneously methyl, ethyl, propyl, butyl, isobutyl, pentyl, hexyl, heptyl, octyl, nonyl, decyl, undecyl, dodecyl, tridecyl, tetradecyl, pentadecyl or hexadecyl.

In another embodiment, X is chloride, bromide, decanoate, (bis 2,4,4-trimethylpentyl)phosphinate, dicyanamide, tosylate, methylsulfate, bistriflamide, hexafluorophosphate, tetrafluoroborate, diethylphosphate or dedecylsulfonate.

In another embodiment, the phosphonium ion salt ionic liquid is tetradecyl(trihexyl)phosphonium chloride, tetradecyl(trihexyl)phosphonium bromide, tetradecyl(trihexyl)phosphonium decanoate, tetradecyl(trihexyl)phosphonium (bis 2,4,4-trimethylpentyl)phosphinate, tetradecyl(trihexyl)phosphonium dicyanamide, triisobutyl(methyl)phosphonium tosylate, tributyl(methyl)phosphonium methylsulfate, tetradecyl(trihexyl)phosphonium bistriflamide, tetradecyl(trihexyl)phosphonium hexafluorophosphate, tetradecyl(trihexyl)phosphonium tetrafluoroborate, tributyl(hexadecyl)phosphonium bromide, tetrabutylphosphonium bromide, tetrabutylphosphonium chloride, tetraoctylphosphonium bromide, tetradecyl(tributyl)phosphonium chloride, ethyltri(butyl)phosphonium diethylphosphate, tetradecyl(tributyl)phosphonium dodecylsulfonate or tetradecyl(trihexyl)phosphonium dodecylsulfonate.

In another embodiment, wherein the phosphonium ion salt ionic liquid is selected from

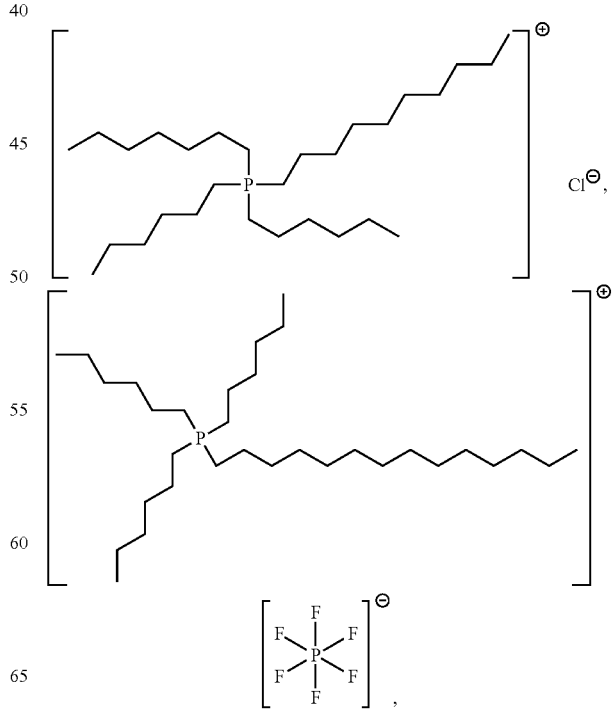

-continued

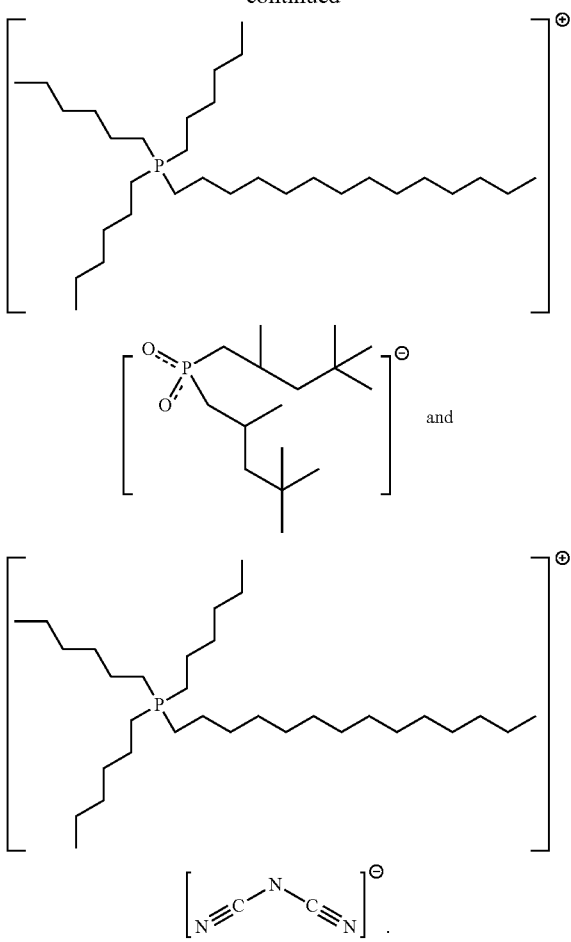

and

In an embodiment of the disclosure, the styrene or styrene derivative monomer unit is a compound of the formula (I)

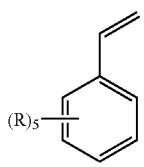

(I)

wherein each R is simultaneously or independently H, halo or $C_{1-4}$alkyl, the latter group being optionally substituted by halo, $C_{1-2}$alkyl or fluoro-substituted $C_{1-2}$alkyl. In a further embodiment, each R is simultaneously or independently H, methyl or ethyl. In another embodiment, each R is H.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The invention will now be described in greater detail with reference to the following drawings in which.

Figure 1:
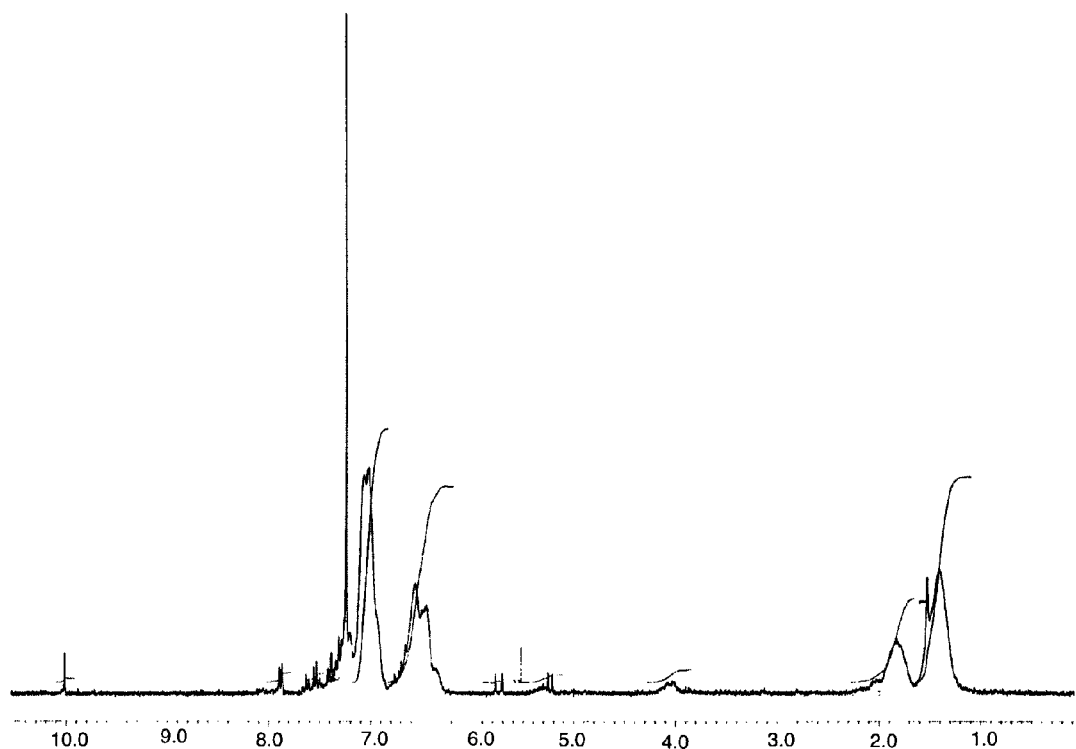
FIG. 1 is an $^1$H NMR spectrum of a polystyrene polymer (A1) produced in accordance with an embodiment of the present disclosure.

DETAILED DESCRIPTION OF THE DISCLOSURE (I) Definitions

The term "$C_{1-n}$alkyl" as used herein means straight and/or branched chain, saturated alkyl radicals containing from one to "n" carbon atoms and includes (depending on the identity of n) methyl, ethyl, propyl, isopropyl, n-butyl, s-butyl, isobutyl, t-butyl and the like, where the variable n is an integer representing the largest number of carbon atoms in the alkyl radical.

The term "halo" as used herein means halogen and includes chloro, fluoro, bromo and iodo.

The term "fluoro-substituted $C_{1-2}$alkyl" as used herein that at least one (including all) of the hydrogens on the referenced group is replaced with fluorine.

The term "styrene monomer units" as used herein means individual monomer units which undergo free radical polymerization to form polystyrene or a polystyrene derivative. In an embodiment, the styrene monomer unit is unsubstituted styrene which polymerizes to form polystyrene. In another embodiment, the styrene monomer unit is substituted in which case, polystyrene derivatives are formed during the polymerization reaction.

The term "phosphonium ion salt ionic liquid" or "phosphonium ion salt" as used herein can be used interchangeably and refer to ionic phosphonium compound which is a liquid at a temperature of less than about 100° C., containing a phosphonium cation and any suitable associated anion. Examples of phosphonium cations include, but are not limited to, trihexyl(tetradecyl)phosphonium, while examples of anions include, but are not limited to halide anions (such as chloride), hexafluorophosphate $(PF_6)^-$, dicyanamide or bis-2,4,4-(trimethylpentyl)phosphinate.

The term "free radical initiator" as used herein means any compound which is able to promote a free radical polymerization of a styrene monomer unit. Accordingly, a free radical initiator possesses a labile bond which generates free radicals when the bond is broken. The free radicals generated by the free radical initiator then promote the free radical polymerization of the styrene monomer units. Examples of free radical initiators include hydrogen peroxide, benzoyl peroxide, azobisisobutyronitrile and the like.

The term "conditions for the polymerization of styrene monomer units" as used herein means any physical or chemical condition in which the polymerization of the styrene monomer units proceeds. In an embodiment, the conditions for the polymerization of the styrene monomer units promote the polymerization reaction. For example, conditions which promote the polymerization of the styrene monomer units include heating the reaction mixture, exposing the reaction mixture to microwave or ultraviolet energy, stirring the reaction mixture, or allowing the polymerization reaction to proceed for a longer period of time than normal to bring the reaction to, or near, completion.

The term "incorporated into" as used herein refers to the phosphonium ion salt ionic liquid being entrained within the polystyrene or polystyrene derivative to form a polystyrene polymer composite. In an embodiment, at least about 1%, about 2%, about 5%, about 10%, about 15%, about 20% or about 25% (mole fraction) of the phosphonium ion salt ionic liquid is incorporated (or entrained) into the structure of the polystyrene or polystyrene derivative during the free radical propagation mechanism.

The term "polystyrene derivative" or "styrene derivative" as used herein refers to derivatives and analogs of the vinylbenzene (styrene). Accordingly, in an embodiment, a styrene derivative is any compound in which the phenyl ring and the vinyl moieties of the styrene molecule possess other groups such as, but not limited to, halo or $C_{1-4}$alkyl.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Processes of the Disclosure

The production of polystyrene and polystyrene derivatives is generally performed in volatile organic solvents. Such solvents pose an environmental issue due to their high volatility. The production of polystyrene and polystyrene derivatives in phosphonium ion salt ionic liquids obviates the need for organic solvents. In addition, the polymerization process of the present disclosure proceeds with up to, and including, 100% efficiency, with incorporation of the phosphonium ion salt ionic liquids into the polymer structure, minimizing the by-products of the process.

Accordingly, the present disclosure relates to a process for the production of polystyrene or a polystyrene derivative from styrene or styrene derivative monomer units in an ionic liquid at pressures at or near atmospheric pressure (1 atm). Further, the process of the present disclosure converts the styrene monomer units to polystyrene with efficiencies of up to, and including, 100%.

Accordingly, the present disclosure includes a process for the production of polystyrene or a polystyrene derivative, comprising polymerizing styrene or styrene derivative monomer units in a phosphonium ion salt ionic liquid in the presence of a free radical initiator at a pressure of about 0.8 to about 1.2 atmospheres, under conditions for the polymerization of styrene or styrene derivative, wherein at least about 1% (mole fraction) of the phosphonium ion salt ionic liquid is incorporated into the polystyrene or polystyrene derivative.

In another embodiment, at least about 2%, about 5%, about 10%, about 15%, about 20% or about 25% (mole fraction) of the phosphonium ion salt ionic liquid is incorporated into the structure of the polystyrene or polystyrene derivative.

In another embodiment, the phosphonium ion salt ionic liquid has the structure:

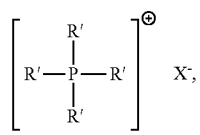

wherein
each R' is independently or simultaneously $C_{1-20}$alkyl and X is any suitable anionic ligand. In another embodiment, each R' is independently or simultaneously methyl, ethyl, propyl, butyl, isobutyl, pentyl, hexyl, heptyl, octyl, nonyl, decyl, undecyl, dodecyl, tridecyl, tetradecyl, pentadecyl or hexadecyl.

In another embodiment, X is chloride, bromide, decanoate, (bis trimethylpentyl)phosphinate, dicyanamide, tosylate, methylsulfate, bistriflamide, hexafluorophosphate, tetrafluoroborate, diethylphosphate or dedecylsulfonate.

In another embodiment, the phosphonium ion salt ionic liquid is tetradecyl(trihexyl)phosphonium chloride, tetradecyl(trihexyl)phosphonium bromide, tetradecyl(trihexyl) phosphonium decanoate, tetradecyl(trihexyl)phosphonium (bis 2,4,4-trimethylpentyl)phosphinate, tetradecyl(trihexyl) phosphonium dicyanamide, triisobutyl(methyl) phosphonium tosylate, tributyl(methyl)phosphonium methylsulfate, tetradecyl(trihexyl)phosphonium bistriflamide, tetradecyl(trihexyl)phosphonium hexafluorophosphate, tetradecyl(trihexyl)phosphonium tetrafluoroborate, tributyl(hexadecyl)phosphonium bromide, tetrabutylphosphonium bromide, tetrabutylphosphonium chloride, tetraoctylphosphonium bromide, tetradecyl(tributyl)phosphonium chloride, ethyltri(butyl)phosphonium diethylphosphate, tetradecyl(tributyl)phosphonium dodecylsulfonate or tetradecyl (trihexyl)phosphonium dodecylsulfonate.

In another embodiment, the phosphonium ion salt ionic liquid is selected from

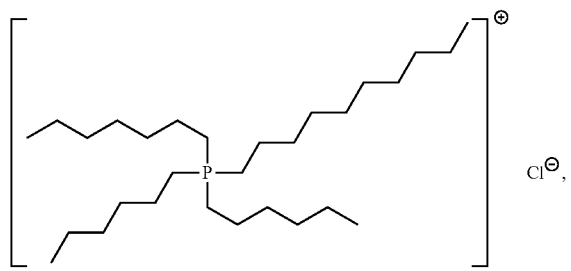

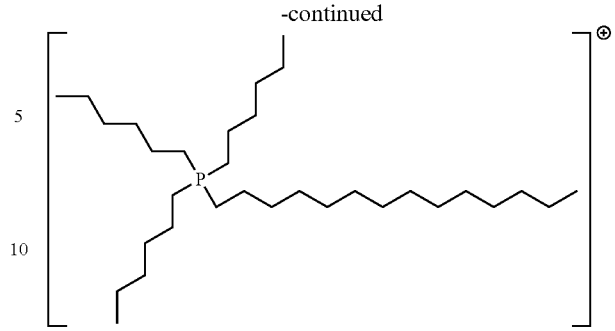

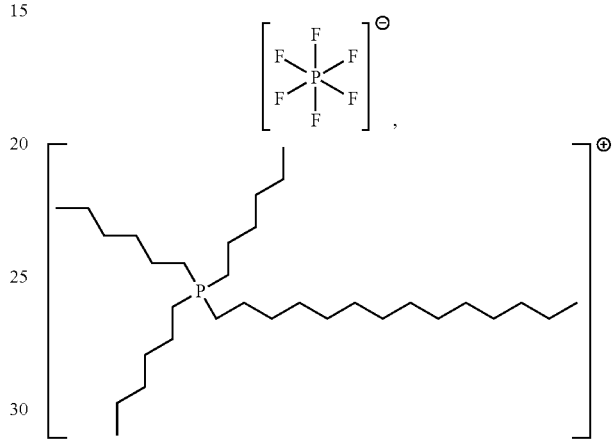

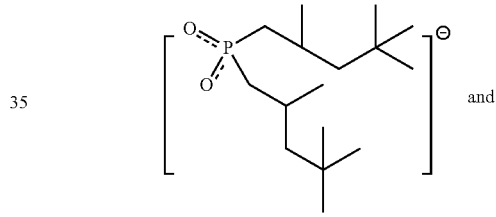

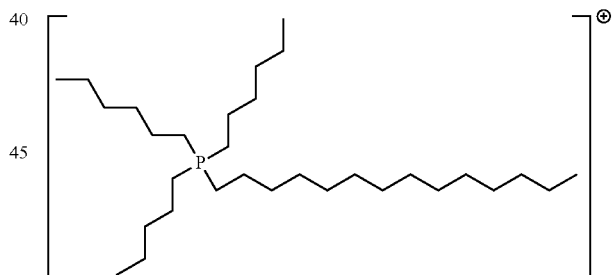

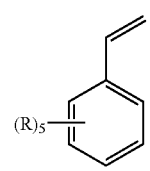

In an embodiment of the disclosure, the styrene or styrene derivative monomer unit is a compound of the formula (I)

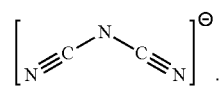

(I)

wherein each R is simultaneously or independently H, halo or $C_{1-4}$alkyl, the latter group being optionally substituted by halo, $C_{1-2}$alkyl or fluoro-substituted $C_{1-2}$alkyl. In a further embodiment, each R is simultaneously or independently H, methyl or ethyl. In another embodiment, each R is H.

In another embodiment of the present disclosure, the free radical initiator is selected from benzoyl peroxide, hydrogen peroxide and azobisisobutyronitrile (AIBN). In another embodiment, the free radical initiator is present in an amount of about 0.05% to about 3% (v/v). In a further embodiment, the free radical initiator is present in an amount of about 0.1% to about 2% (v/v). In an embodiment of the disclosure, the rate of the polymerization reaction is increased when a free radical initiator is used in the reaction, as opposed to when no free radical initiator is added which slows the rate of the polymerization.

In a further embodiment of the present disclosure, the polymerization is performed at a pressure of about 0.9 to about 1.1 atmospheres. In another embodiment, the polymerization is performed at a pressure of about 1.0 atmosphere. In another embodiment, the polymerization is performed at about atmospheric pressure. It will be understood by those skilled in the art that atmospheric pressure changes with altitude. In another embodiment of the disclosure, the polymerization reaction is performed at a pressure, suitably about atmospheric pressure, which allows the reaction to be performed in an open system without the application of a vacuum.

In an embodiment, the polymerization processes of the present disclosure proceed through a free radical based propagation mechanism. It will be known to those skilled in the art that molecular oxygen ($O_2$), being a free radical, can terminate the propagation of the polymerization reaction. Accordingly, such polymerization reactions are often conducted under high vacuum to exclude oxygen, which adds time and expense. In another embodiment of the disclosure, due to the viscosity of phosphonium ion salt ionic liquid, molecular oxygen ($O_2$) cannot diffuse quickly through the ionic liquid, and therefore does not act as effectively as a chain terminator. Accordingly, in an embodiment, the processes of the present disclosure do not need to be performed under vacuum to exclude oxygen.

In an embodiment, the conditions for the polymerization of polystyrene comprise a temperature of about 10° C. to about 150° C. In a further embodiment, the conditions for the polymerization of polystyrene comprise a temperature of about 25° C. to about 80° C. In another embodiment, the conditions for the polymerization of polystyrene comprise a temperature of about 25° C. In an embodiment of the disclosure, the polymerization reaction proceeds with a faster rate of reaction as the temperature increases. Accordingly, the rate of the polymerization reaction is much faster at a temperature of 100° C. than at a temperature of 10° C. In another embodiment, when the polymerization reaction is performed at a higher temperature, such as at 100° C., the resulting polystyrene polymer is physically much harder than when the reaction is performed at a lower temperature, such as 10° C., which yields softer polymers. Accordingly, a person skilled in the art is able to manipulate the physical characteristics of the polystyrene polymer by performing the polymerization reaction at different temperatures.

In a further embodiment of the present disclosure, the conditions for the polymerization of styrene or styrene derivative monomer units comprise a mole fraction ratio of the styrene or styrene derivative monomer units to the phosphonium ion salt ionic liquid of about 0.10:1.0 to about 2.0: 1.0 (styrene or styrene derivative monomer units:ionic liquid). In a further embodiment of the present disclosure, the conditions for the polymerization of the styrene or styrene derivative monomer units comprise a mole fraction ratio of the styrene or styrene derivative monomer units to the phosphonium ion salt ionic liquid of about 0.10:1.0 to about 1.0: 1.0 (styrene or styrene derivative monomer units:ionic liquid). In another embodiment, the conditions for the polymerization of styrene or styrene derivative monomer units comprise a mole fraction ratio of the styrene or styrene derivative monomer units to the phosphonium ion salt ionic liquid of about 0.11:1.0 to about 0.33:1.0 (styrene or styrene derivative monomer units:ionic liquid). In an embodiment of the disclosure, increasing the mole fraction ratio of the styrene or styrene derivative monomer units increases the rate of the polymerization reaction.

In another embodiment of the disclosure, water is added to the reaction mixture. In an embodiment, the addition of water to the reaction mixture results in a more evenly stirred and more evenly heated reaction mixture, and consequently, results in physically harder polystyrene polymers.

In an embodiment of the disclosure, the conditions for the polymerization of styrene or styrene derivative monomer units comprise microwave energy. In an embodiment, when the polymerization reaction mixture is exposed to microwave energy, the resultant polystyrene polymers are physically much harder than when microwave energy is not employed. Accordingly, a person skilled in the art is able to control the physical properties, in particular the hardness, of the polystyrene polymer by exposing the reaction mixture to microwave energy. Furthermore, by controlling the power of the microwave energy and the amount of time the reaction mixture is exposed to the microwave energy, a person skilled in the art is able to control the physical properties of the polystyrene polymer, in particular the hardness of the polymer. In another embodiment, when the reaction mixture is exposed to microwave energy, the resultant polystyrene or polystyrene derivatives possesses a brown color.

In another embodiment, the conditions for the polymerization of styrene or styrene derivative monomer units comprise ultraviolet light. In another embodiment, the ultraviolet light is derived from sunlight. In an embodiment of the disclosure, the rate of the polymerization reaction is increased upon exposing the reaction mixture to sunlight. Accordingly, in an embodiment, when the polymerization reaction is performed without the addition of heat (thermal energy), sunlight or ultraviolet light is used to promote the polymerization reaction.

In another embodiment of the disclosure, the polymerization reaction is performed in a vessel, in which the vessel is equipped with a stirrer, such as magnetic stirrer. In an embodiment, when the polymerization reaction proceeds with fast stirring, the rate of the polymerization is increased, and subsequently, yields physically harder polystyrene polymers, as opposed to slow stirring which yields softer polymers and a slower the polymerization reaction. Accordingly, a person skilled in the art is able to manipulate the physical characteristics of the polystyrene polymer by controlling the rate of stirring in the vessel in which the polymerization reaction is performed.

In another embodiment of the disclosure, the process proceeds by the precipitation out of the ionic liquid of the polystyrene or polystyrene derivative, as the polystyrene or polystyrene derivative composite is insoluble in the ionic liquid. Accordingly, liquid on top of the precipitated product is unreacted which can be subsequently decanted from the reactor and further reacted to form more product, with this process repeated until the starting materials are consumed. Accordingly, as the ionic liquid is incorporated into the polymeric structure of the polystyrene or polystyrene derivative, there is no waste by-product.

In another embodiment of the disclosure, the process proceeds with 100% efficiency of converting the styrene or styrene derivative monomer units into polystyrene or polystyrene derivative with no associated waste of materials, as the phosphonium ion salt ionic liquid is incorporated into the polymer. Accordingly, in an embodiment of the disclosure, when the process proceeds with 100% efficiency, the phosphonium ion salt is absorbed into the structure of the polystyrene derivative, and consequently, the polymerization proceeds with no waste.

(III) Polymer Composites of the Disclosure

The present disclosure includes a polymer composite comprising a polystyrene or a polystyrene derivative in which at least about 1%, about 2%, about 5%, about 10%, about 15%, about 20% or about 25% (mole fraction) of a phosphonium ion salt ionic liquid is incorporated into the structure of the polystyrene or polystyrene derivative.

In another embodiment, the styrene or styrene derivative monomer unit is a compound of the formula (I)

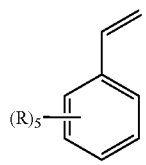

(I)

wherein
each R is simultaneously or independently H, halo or $C_{1-2}$alkyl, the latter group being optionally substituted by halo, $C_{1-2}$alkyl or fluoro-substituted $C_{1-2}$alkyl. In a further embodiment, each R is simultaneously or independently H, methyl or ethyl. In another embodiment, each R is H.

In another embodiment, the phosphonium ion salt has the structure:

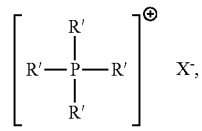

wherein
each R' is independently or simultaneously $C_{1-20}$alkyl and X is any suitable anionic ligand. In another embodiment, each R' is independently or simultaneously methyl, ethyl, propyl, butyl, isobutyl, pentyl, hexyl, heptyl, octyl, nonyl, decyl, undecyl, dodecyl, tridecyl, tetradecyl, pentadecyl or hexadecyl.

In another embodiment, X is chloride, bromide, decanoate, (bis 2,4,4-trimethylpentyl)phosphinate, dicyanamide, tosylate, methylsulfate, bistriflamide, hexafluorophosphate, tetrafluoroborate, diethylphosphate or dedecylsulfonate.

In another embodiment, the phosphonium ion salt ionic liquid is tetradecyl(trihexyl)phosphonium chloride, tetradecyl(trihexyl)phosphonium bromide, tetradecyl(trihexyl)phosphonium decanoate, tetradecyl(trihexyl)phosphonium (bis 2,4,4-trimethylpentyl)phosphinate, tetradecyl(trihexyl) phosphonium dicyanamide, triisobutyl(methyl) phosphonium tosylate, tributyl(methyl)phosphonium methylsulfate, tetradecyl(trihexyl)phosphonium bistriflamide, tetradecyl(trihexyl)phosphonium hexafluorophosphate, tetradecyl(trihexyl)phosphonium tetrafluoroborate, tributyl(hexadecyl)phosphonium bromide, tetrabutylphosphonium bromide, tetrabutylphosphonium chloride, tetraoctylphosphonium bromide, tetradecyl(tributyl)phosphonium chloride, ethyltri(butyl)phosphonium diethylphosphate, tetradecyl(tributyl)phosphonium dodecylsulfonate or tetradecyl (trihexyl)phosphonium dodecylsulfonate.

In a further embodiment, the phosphonium ion salt is selected from

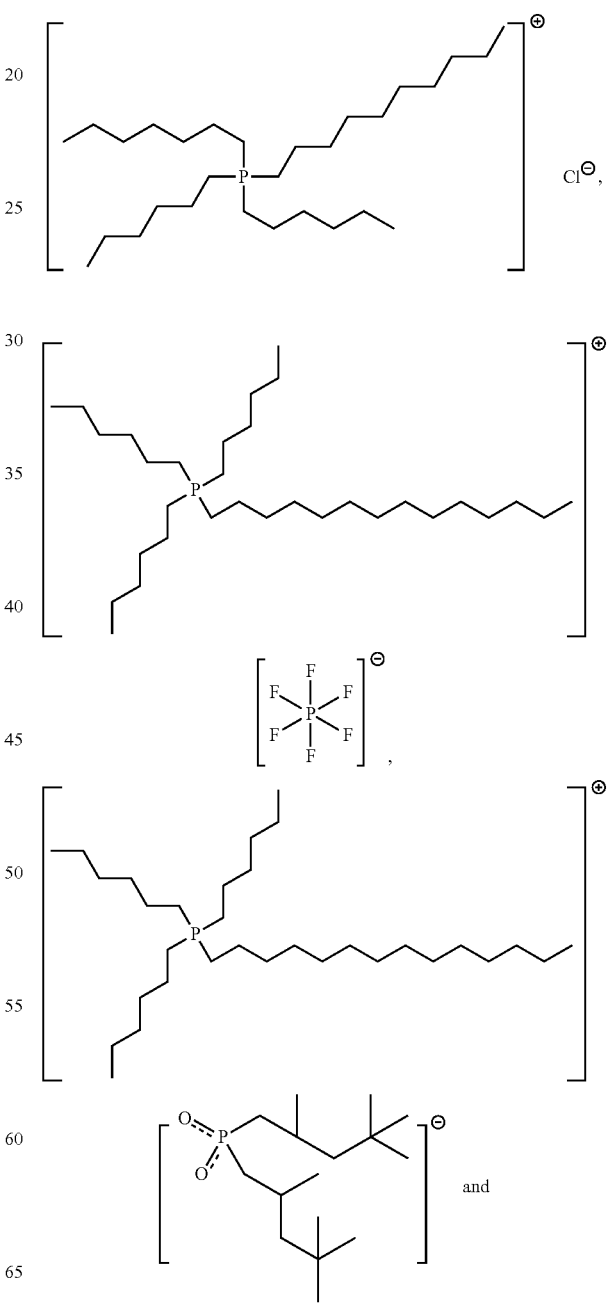

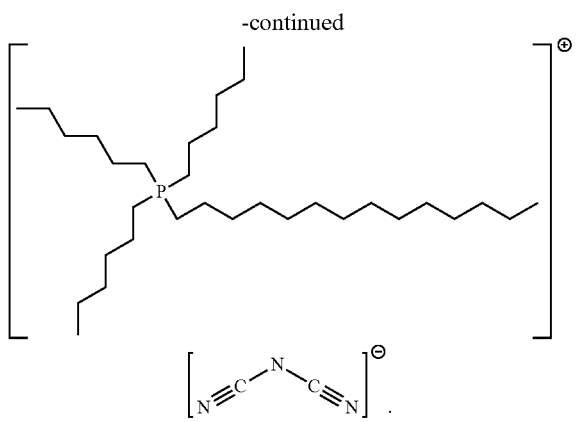

In an embodiment of the disclosure, and as a result of the phosphonium ion salt being absorbed into the structure of the polystyrene or polystyrene derivative, the ionic nature of the phosphonium ion salt results in polystyrene polymers or polystyrene derivatives which are able to conduct electricity much better than normal polystyrene. Accordingly, also included within the scope of the disclosure, are polystyrene polymers (or derivatives) embedded with phosphonium ion salts, in which the phosphonium ion salts are as defined above. In an embodiment, when the phosphonium ion salts are incorporated into the polystyrene and polystyrene derivatives, novel polystyrene and polystyrene derivative composites are produced.

Figure 30:
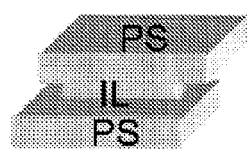
FIG. 30 is a schematic representation of a polymer composite in an embodiment of the present disclosure.

In another embodiment, and without being bound by theory, it is believed that the polymer composites of the present disclosure possess a structure, for example, as shown in FIG. 30.

In another embodiment, the polymer compound comprising a polystyrene or a polystyrene derivative the phosphonium ion salt, further comprises a metal dopant. In another embodiment, the selection of the metal dopant is any metal which influences the strength, conductivity or magnetic properties of the polymer composites. In another embodiment, the metal dopant is a magnetic metal, such as copper or iron. In another embodiment, the metal dopant comprises gold nanoparticles. In an embodiment, the phosphonium ion salt ionic liquids of the present disclosure do not bond or interfere with the metal dopants, for example, as shown in the following schematic of a gold/polymer composite.

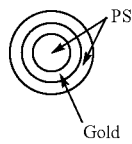

In another embodiment, the polymer composites, are useful as sensors, actuators, catalysts and scintillators.

In another embodiment, the polymer composites of the present disclosure are useful for making high pressure nuclear magnetic resonance (NMR) sample holders as well as magnetic resonance imaging (MRI) instruments, as well as electronic circuits and magnetic screens.

In another embodiment, the polymer composites of the present disclosure are useful for producing electronic circuits due to the conductive paths of phosphonium ion salt in the polymer composite.

In another embodiment, the polymer composites of the present disclosure are useful for producing polystyrene-based composites having metallic properties, such as magnetic properties.

In another embodiment of the disclosure, dopants are added to the polymerization reaction, which therefore alters the physical and chemical characteristics of the resulting polystyrene polymer. For example, metal dopants, for example gold nanoparticles, are added to the polymerization reaction. In an embodiment of the disclosure, the addition of metal dopants results in polystyrene polymers that are magnetic and/or conduct electricity. In another embodiment, the dopant is a photosensitizer, which alters the optical properties of the polystyrene polymer, for example, changing the color of the polymer.

The following non-limiting examples are illustrative of the present invention:

EXAMPLES

Materials.

Pure IL 101® (trihexyl(tetradecyl)phosphonium chloride) (with less than 5% water) was bought from Cytec Company. 90% $H_2O_2$ in water was bought from Sigma Aldrich. Solvent grade methanol was used for washing polymers. Styrene was purified by passing it through a silica column or by extracting with sodium hydroxide. All $^1H$ and $^{13}C$ NMR chemical shifts are reported in ppm relative to tetramethylsilane. Pulse widths were 30° for $^{13}C$, 45° for $^1H$ spectra and 35° for $^{31}P$ spectra. Relaxation delays were 0.3 s for $^{13}C$ and 2 s for $^1H$ spectra. Typically, 3000-6150 scans were accumulated for $^{13}C$ spectra, and 32-128 scans for $^1H$ and $^{31}P$ spectra. The spectra were obtained with a 5-mm dual-tune high-resolution probe, with 25-Hz spinning about the z-axis.

Example 1

Preparation of Polystyrene (Polymer A1) in IL-101

Figure 2:
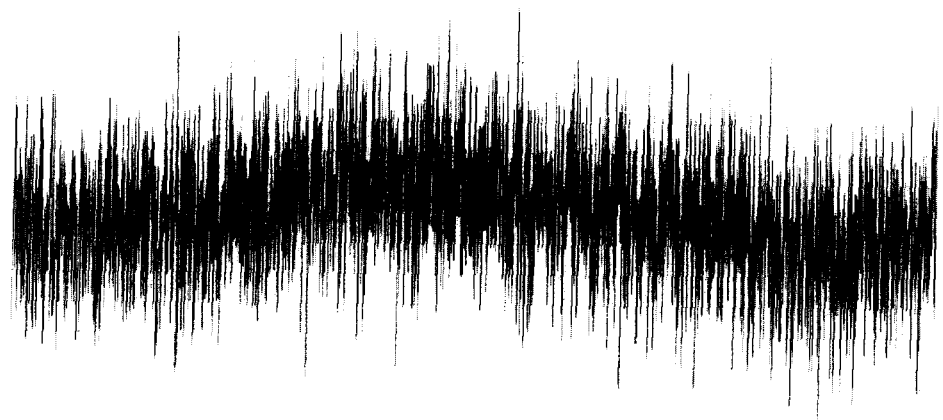
FIG. 2 is a $^{31}$P NMR spectrum of a polystyrene polymer (A1) produced in accordance with an embodiment of the present disclosure.
Figure 3:
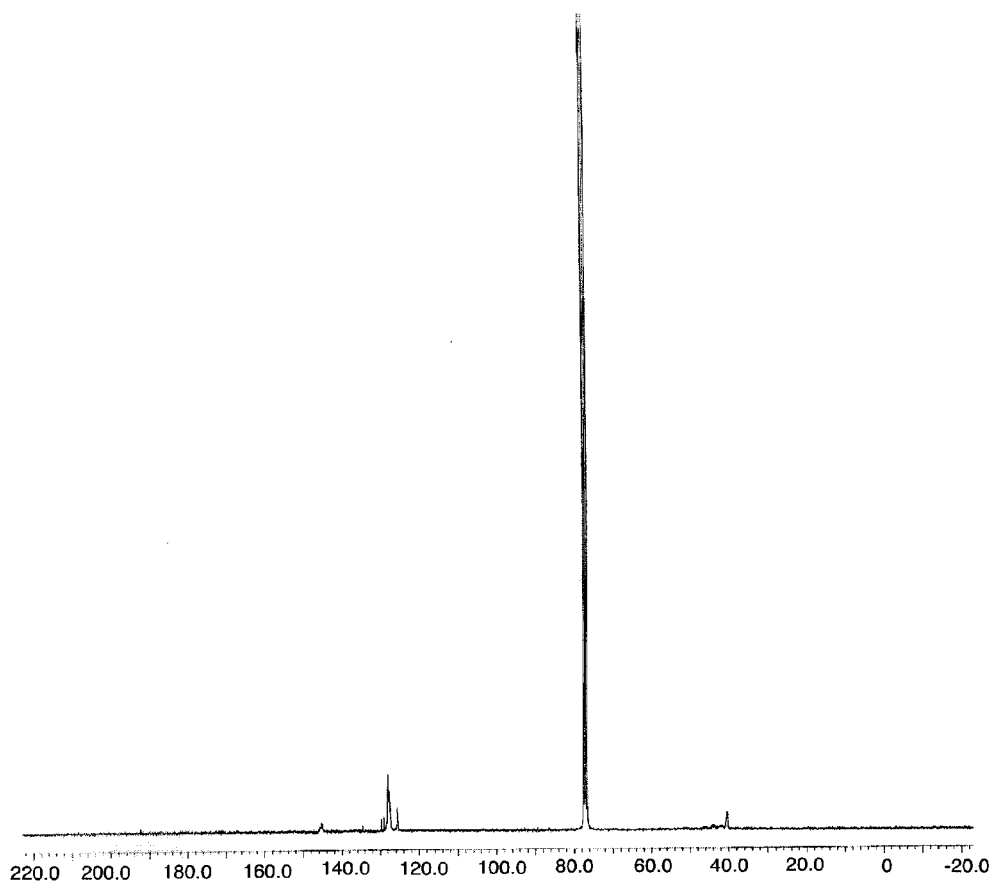
FIG. 3 is a $^{13}$C NMR spectrum of a polystyrene polymer (A1) produced in accordance with an embodiment of the present disclosure.

Polymerizations were performed in a 10 mL Erlenmeyer. The Erlenmeyer was first charged with 1.7137 g IL-101, and then 2.00 mL styrene via pipette. The Erlenmeyer was then put into a 109° C. oil bath for 10 minutes to equilibrate which formed a homogeneous solution. 50 μL $H_2O_2$ was then added. This led to a cloudy solution after 10 minutes. A significant amount of polymer formed on bottom after 1 hour. After 105 minutes, two separate layers formed, yellowish at top, white at bottom. The reaction was stopped after 200 minutes. The yield of this polystyrene polymer (Polymer A1) was 40%. The polymer is a white solid, which was dissolved in deuterated chloroform for NMR analysis, a spectrum for which is shown in FIG. 1. A residual amount of styrene monomer remained within the polymer. The spectrum is suggestive of atactic polystyrene.[13] FIG. 2 shows the $^{31}P$ NMR spectrum for Polymer A1, with shows that no ionic liquid was incorporated within the polymer, while FIG. 3 is a $^{12}C$ NMR spectrum of Polymer A1.

Example 2

Preparation of Polystyrene (Polymer A2) in IL 101

Polymerizations were performed in a in a 10 mL Erlenmeyer. The Erlenmeyer was first charged with 1.7771 g of IL 101, and then 2.00 mL styrene via pipette. The Erlenmeyer was then put into a 64° C. oil bath for 10 minutes to equilibrate which formed a homogeneous solution. Then 50 μL of $H_2O_2$ was added. This lead to a cloudy solution after 240 minutes.

Figure 4:
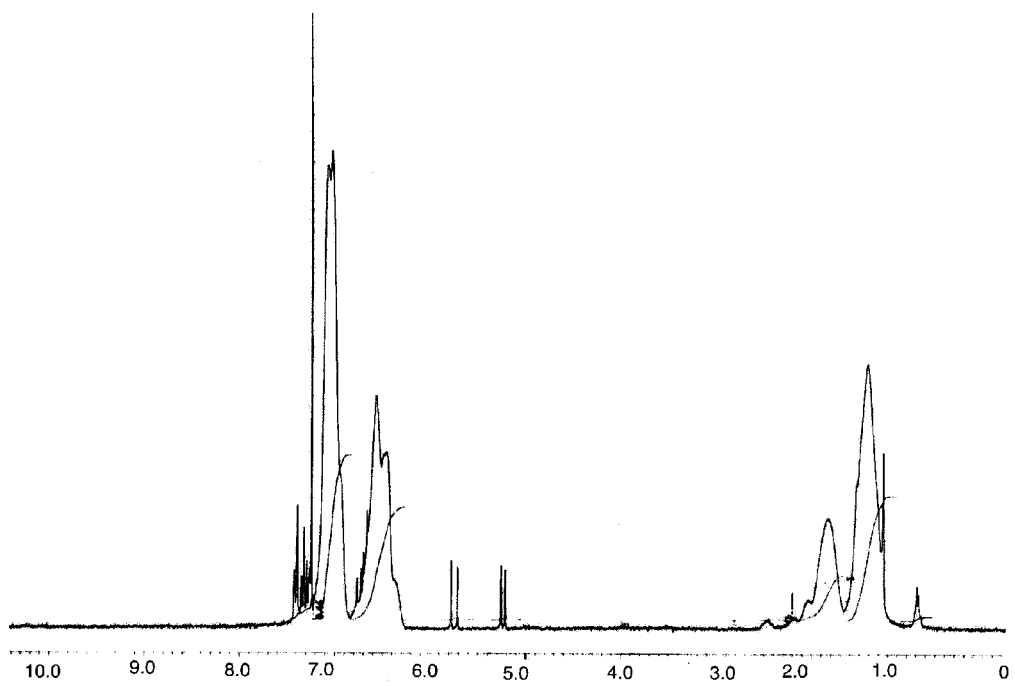
FIG. 4 is an $^1$H NMR spectrum of a polystyrene polymer (A2) produced in accordance with an embodiment of the present disclosure.
Figure 5:
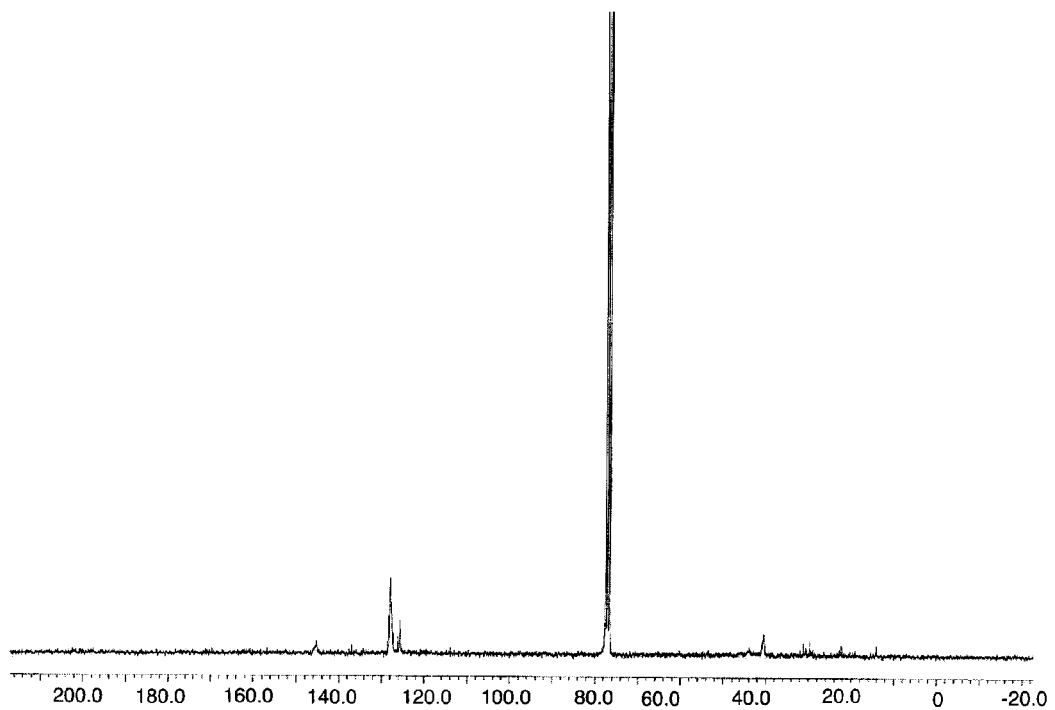
FIG. 5 is a $^{13}$C NMR spectrum of a polystyrene polymer (A2) produced in accordance with an embodiment of the present disclosure.
Figure 6:
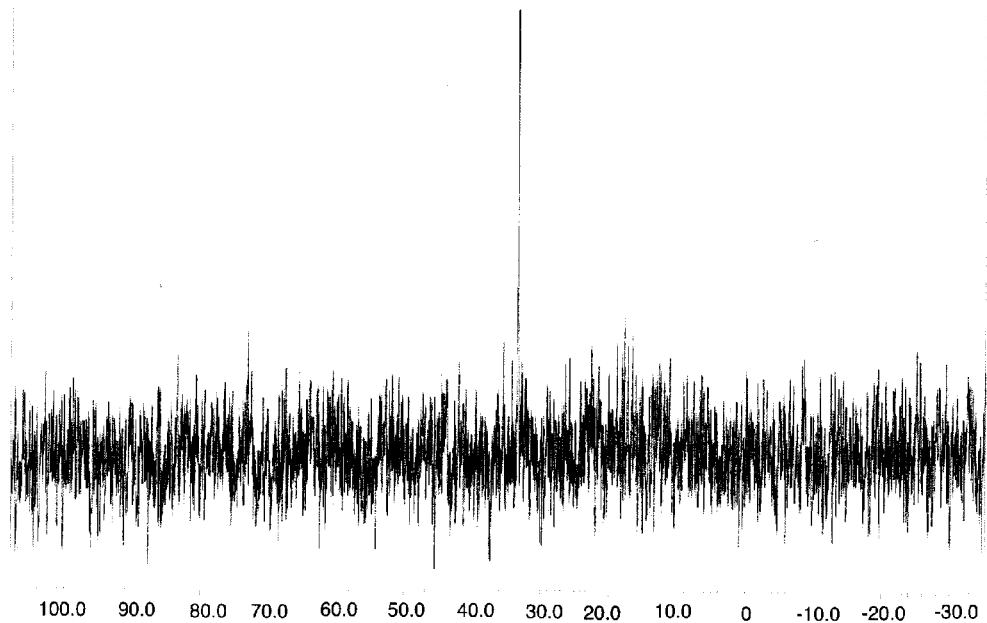
FIG. 6 is a $^{31}$P NMR spectrum of a polystyrene polymer (A2) produced in accordance with an embodiment of the present disclosure.

The heat was increased to 104° C. while stirring for 20 minutes, and the decanted liquid was saved and used in Example 3. The NMR spectra of the Polymer A2 (a white solid) in CDCl$_3$ are presented in FIGS. 4-6 (H-NMR, $^{13}$C-NMR and $^{31}$P-NMR). A residual amount of styrene monomer remained within the polymer. The spectrum is atactic polystyrene with phosphonium cations and chloride anions in between aromatic rings. The yield for polymer A2 was 60%.

Discussion

While proton NMR and carbon NMR show existence of a polystyrene polymer, there are other features that are due to the presence of phosphonium cation, and the existence of the negative ion (chloride). Phosphorous NMR confirms presence of phosphorous, peak at 33.5 ppm. The chemical shift is very similar to the chemical shift of the phosphonium ionic liquid with one phosphorous peak. The ion incorporation is 1%.

Example 3

Preparation of Polystyrene (Polymer A2) from Decanted Liquid

The decanted liquid from Example 2 was heated to 115° C. with a stir rod, after which all of the water boiled off after 30 minutes. This left a hard white polymer, as well as a monomer saturated ionic liquid layer solution. After removing the hard polymer (A3), and washing two times with methanol, the A3 was obtained in 15% yield. According, the total yield of Examples 2 and 3 is 75%.

Figure 7:
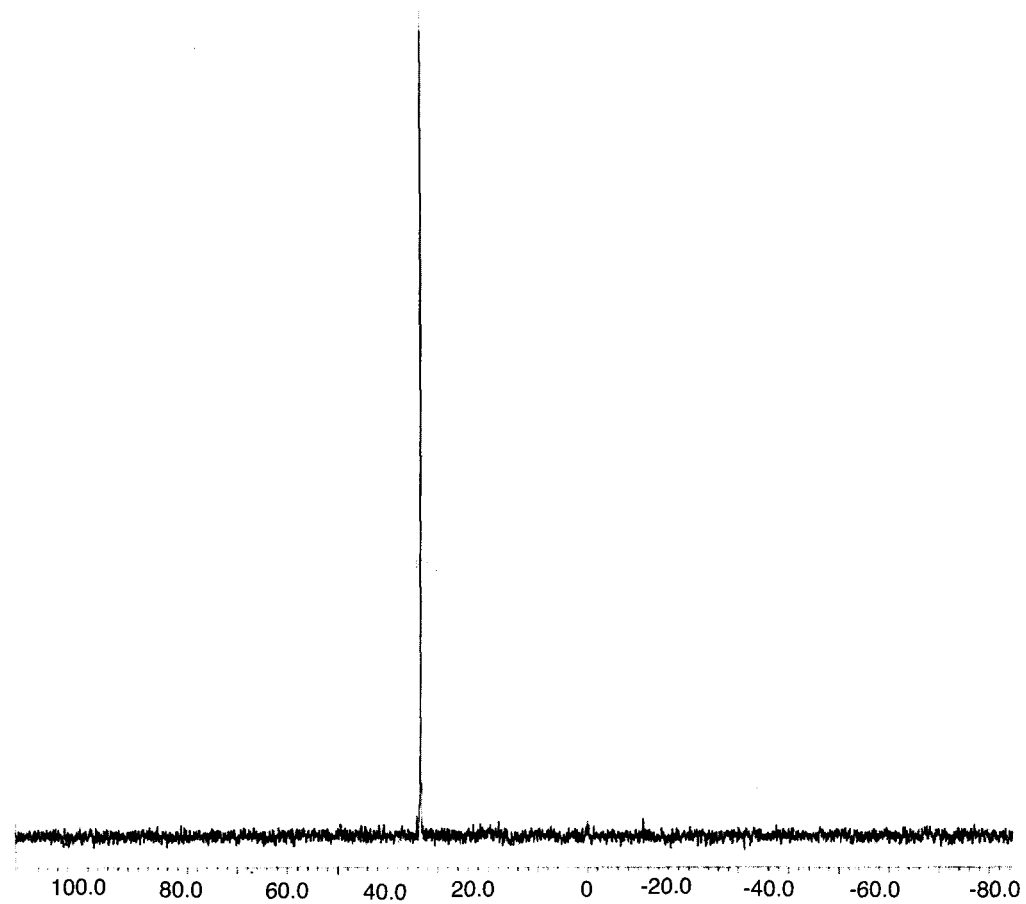
FIG. 7 is a $^{31}$P NMR spectrum of a polystyrene polymer (A3) produced in accordance with an embodiment of the present disclosure.
Figure 8:
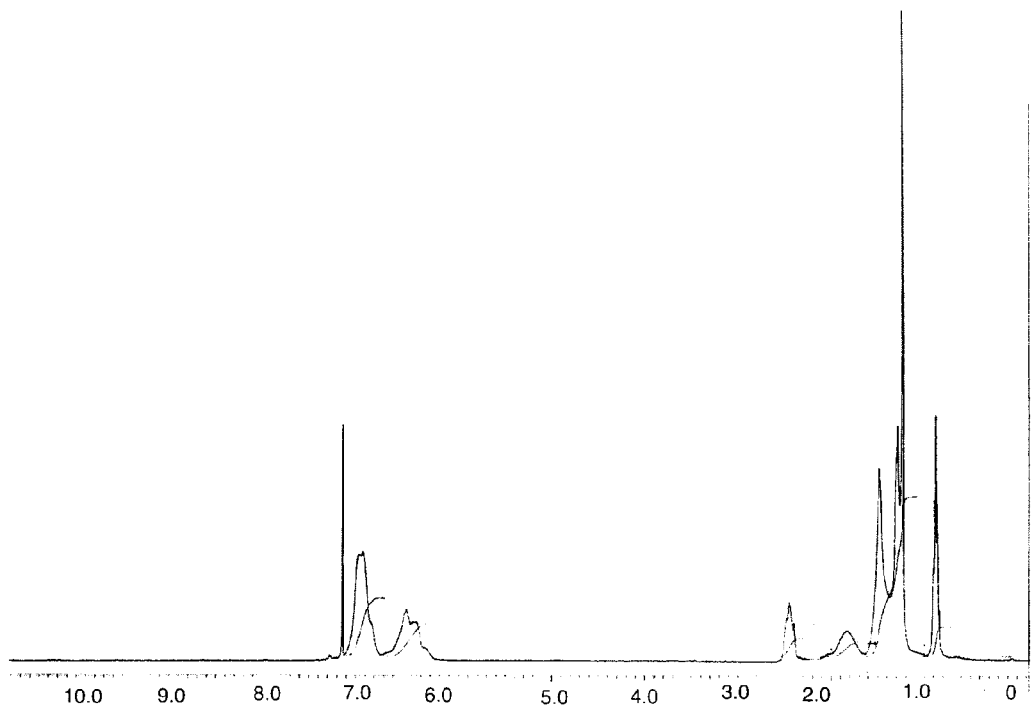
FIG. 8 is an $^1$H NMR spectrum of a polystyrene polymer (A3) produced in accordance with an embodiment of the present disclosure.

As seen in FIG. 7, $^{31}$P-NMR confirms presence of phosphorous, with a peak at 33.5 ppm. A proton NMR spectrum of polymer A3 is shown in FIG. 8. The structure of the polymer is the same as A2, but with 5% ionic incorporation.

Example 4

Preparation of Polystyrene Polymers D1 and D2

The preparation of polystyrene D1 and D2 was performed as a batch type experiment, with additional styrene added every hour. Accordingly, two beakers were labelled D1 and D2 and 4.4988 g and 4.4066 g of IL-101, respectively was placed in each beaker. Styrene was then added to the beakers D1 and D2 in the amounts of 0.8921 g and 0.8958 g to D1 and D2 respectively. After allowing the samples to equilibrate in a hot water bath for 10 minutes at 75° C., 100 μL of H$_2$O$_2$ was added to each. The following amounts of styrene were then added to each beaker after the indicated times:
1) after one hour, 1.0999 g styrene was added to D1, and 0.8920 g styrene to D2. Another 100 μL of H$_2$O$_2$ was added only to D1.
2) after another hour, 0.9090 g styrene was added to D1, and 1.0868 g styrene to D2. Another 100 μL of H$_2$O$_2$ was added only to D1.
3) after a final hour, 10.9031 g styrene was added to D1, and 0.9042 g styrene to D2. Another 100 μL of H$_2$O$_2$ was added only to D1.

Figure 9:
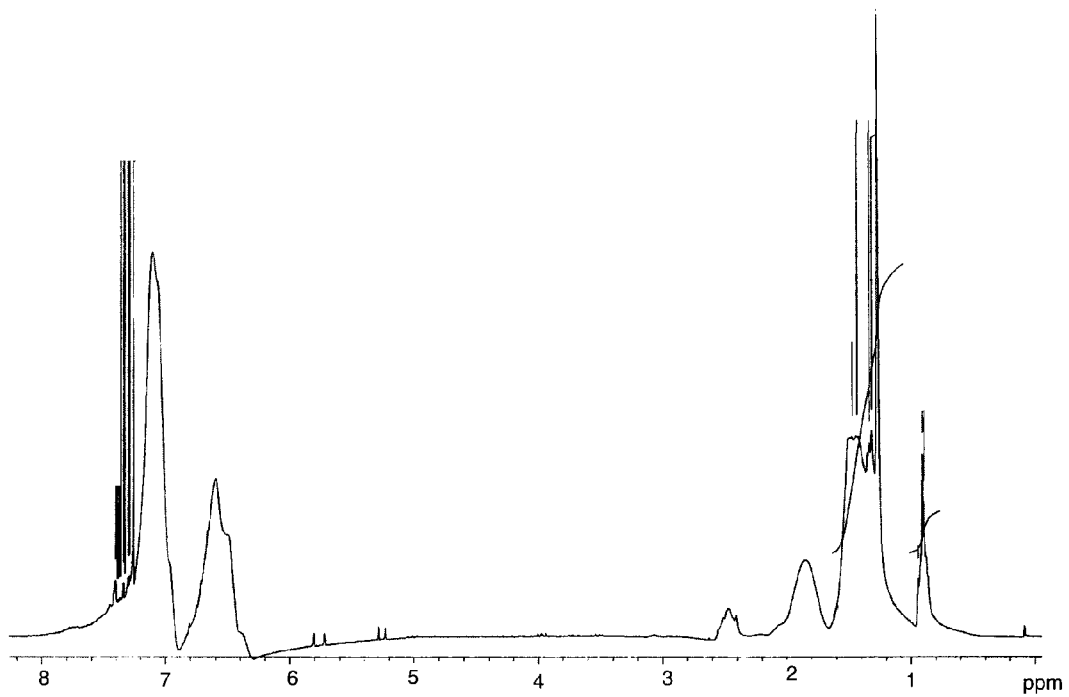
FIG. 9 is an $^1$H NMR spectrum of a polystyrene polymer (D1) produced in accordance with an embodiment of the present disclosure.
Figure 10:
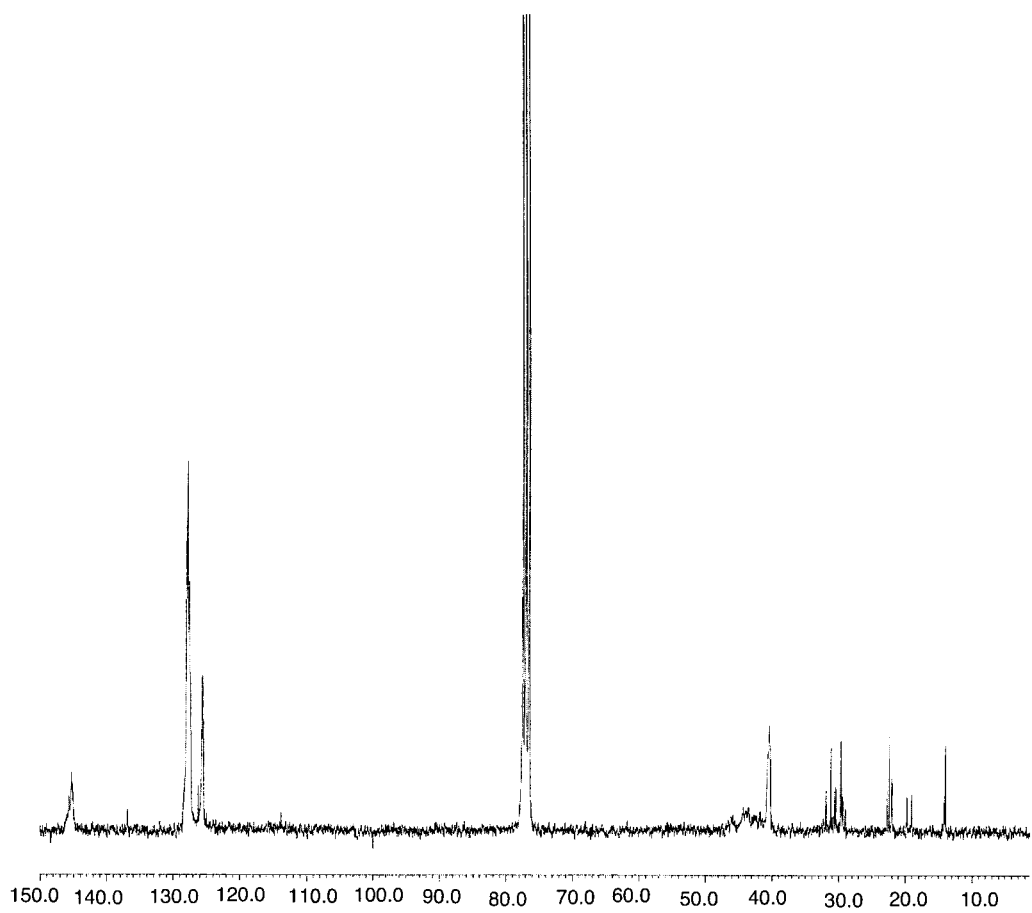
FIG. 10 is a $^{13}$C NMR spectrum of a polystyrene polymer (D1) produced in accordance with an embodiment of the present disclosure.
Figure 11:
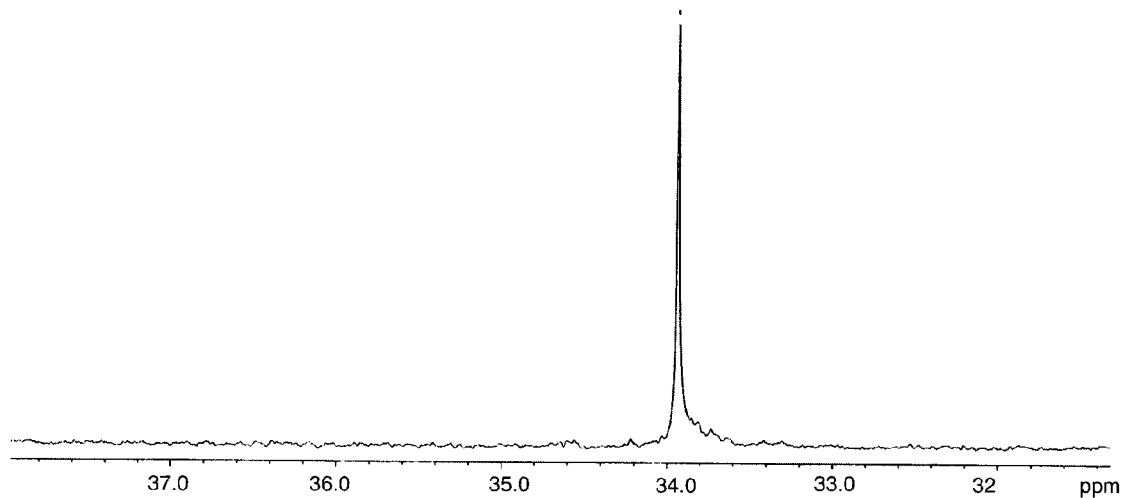
FIG. 11 is a $^{31}$P NMR spectrum of a polystyrene polymer (D1) produced in accordance with an embodiment of the present disclosure.
Figure 12:
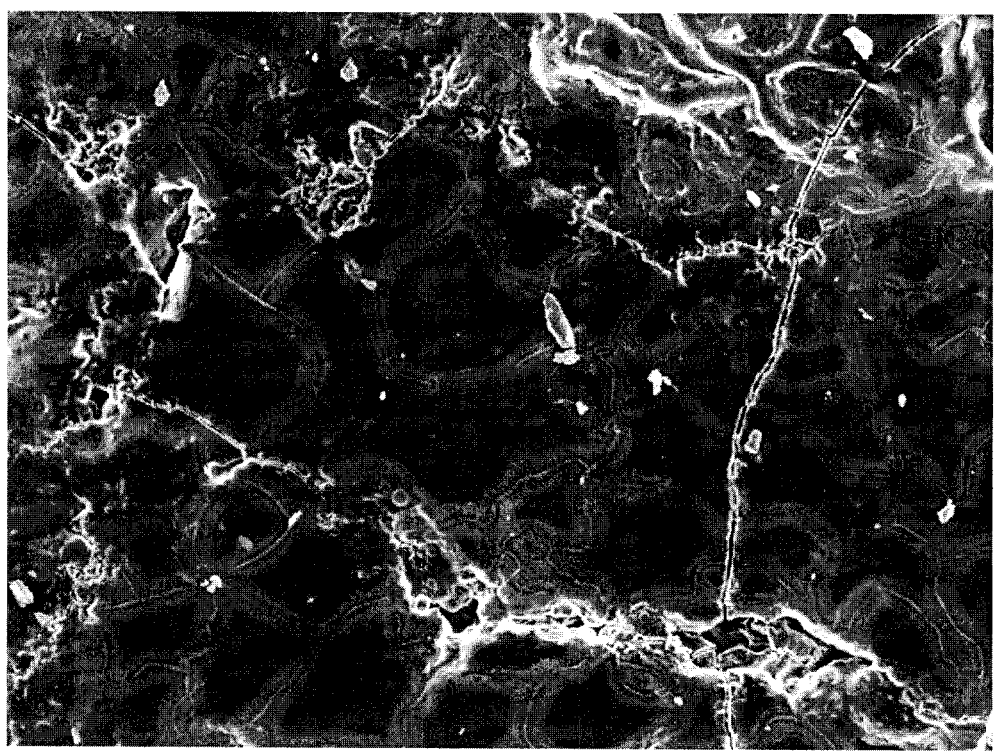
FIG. 12 is a scanning electron micrograph (SEM) of a polystyrene polymer (D1) produced in accordance with an embodiment of the disclosure.
Figure 15:
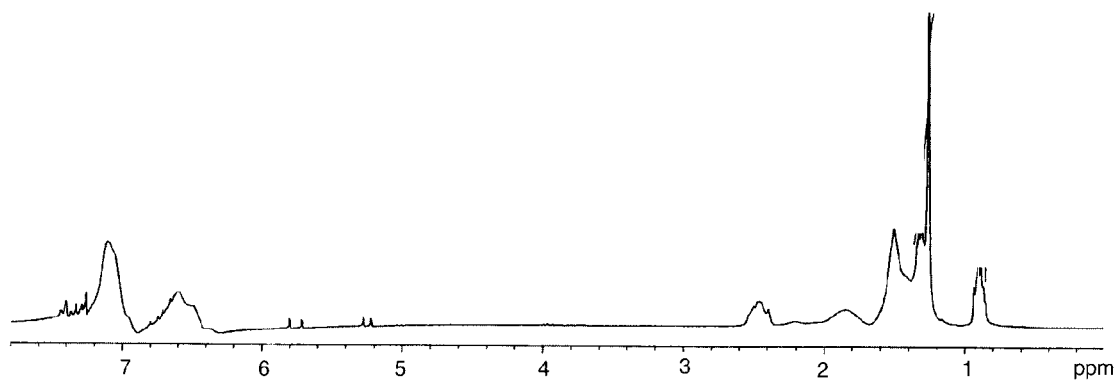
FIG. 15 is an $^1$H NMR spectrum of a polystyrene polymer (D2) produced in accordance with an embodiment of the present disclosure.

The solutions were mixed thoroughly after each addition, but not stirred continuously. Large amounts of polymer formed on the bottom of the beakers after a couple of hours. Beaker D1 then underwent heating at 80° C. in and oven. The resulting D1 polymer was nearly clear crystalline, opaque, extremely hard, and brittle. In the case of D1, the yield was 30%. In the case of D2, after washing with methanol and suction filtration, the yield was 50% (dry powder). The NMR spectra of the polymer D1 in CDCl$_3$ are shown in FIGS. 9-11 (H-NMR and $^{31}$P-NMR). The ion inclusion (from the ionic liquid) is 15% in the polymer D1. FIG. 15 shows the SEM image of Polymer D1, in which there are pathways of lines that cover the sample, which are placements of high concentration of ions within the polymer. In an embodiment, the channels of high ion concentration is exploited to produce conductive channels within a plastic for the production of electronic devices within plastics.

The following table gives the rough percentage of atoms within the polymer D1 for both dark and light areas, based on X-ray fluorescence.

| E1(First session) | | | | | |
|---|---|---|---|---|---|
| Location | C | O | P | Cl | Total |
| Dark area | 95.95 | 2.4 | 1 | 0.65 | 100 |
| Light area | 95.34 | 2.29 | 1.3 | 1.07 | 100 |

Figure 13:
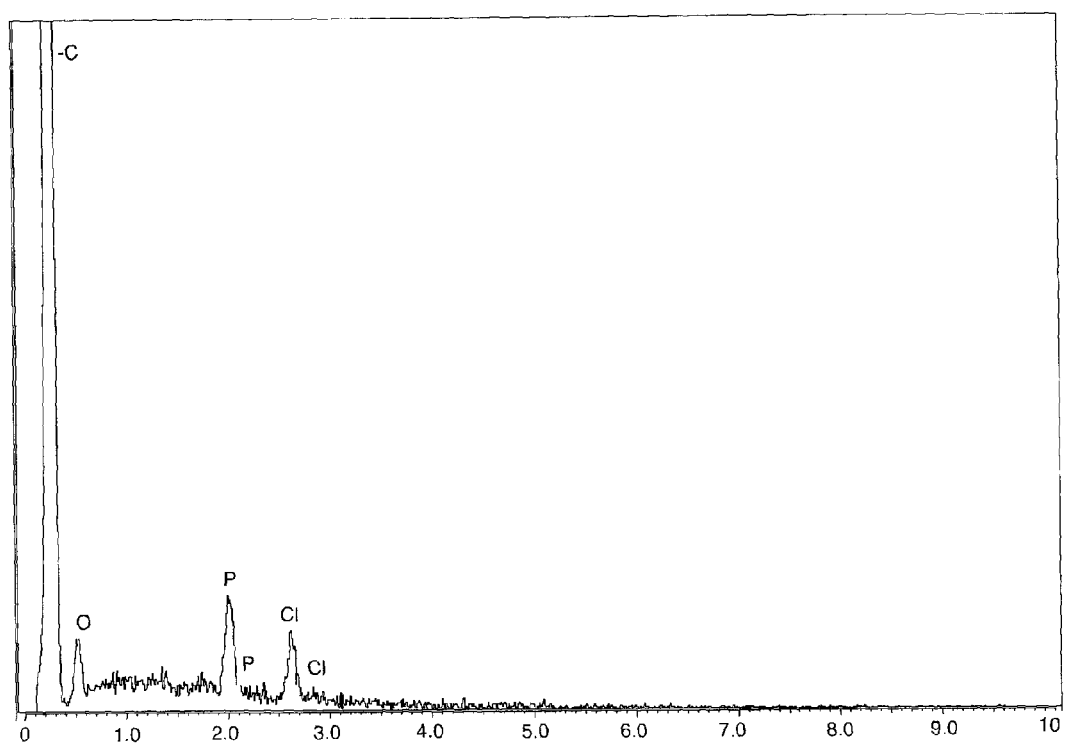
FIG. 13 is an X-ray fluorescence graph of the light portions of the SEM of FIG. 12 of a polystyrene polymer (D1) produced in accordance with an embodiment of the disclosure.
Figure 14:
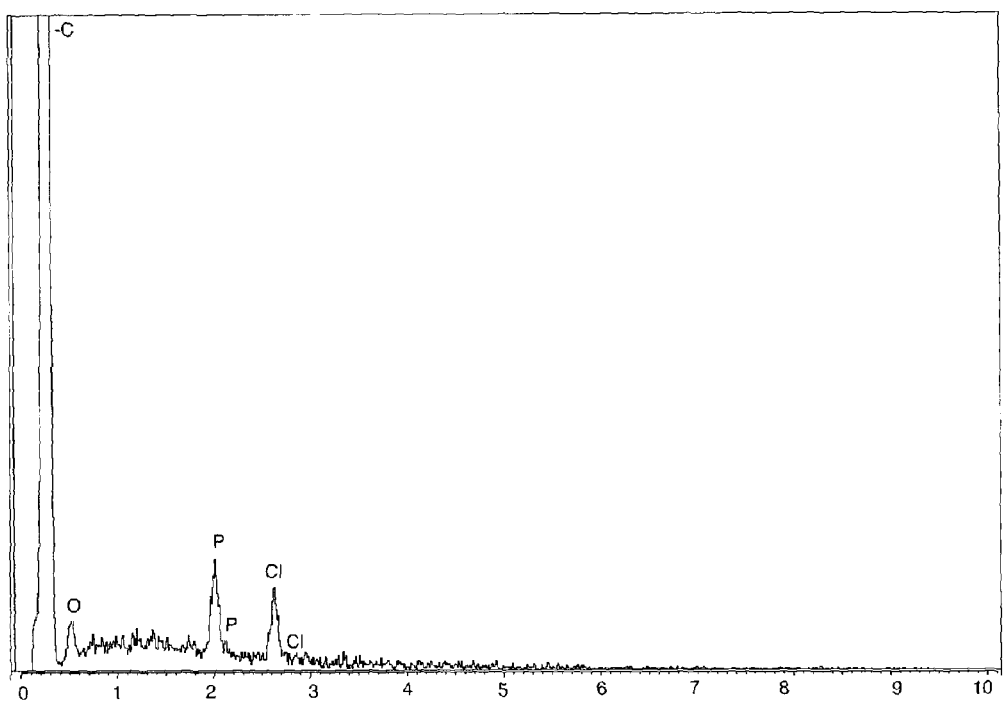
FIG. 14 is an X-ray fluorescence graph of the dark portions of the SEM of FIG. 12 of a polystyrene polymer (D1) produced in accordance with an embodiment of the disclosure.

It is clear that the lighter area has more ionic content. The lowest limit of the ionic content of the polymer in the light area is 15 percent (see FIGS. 13 and 14 for X-ray fluorescence on dark and light parts of the SEM image).

Figure 16:
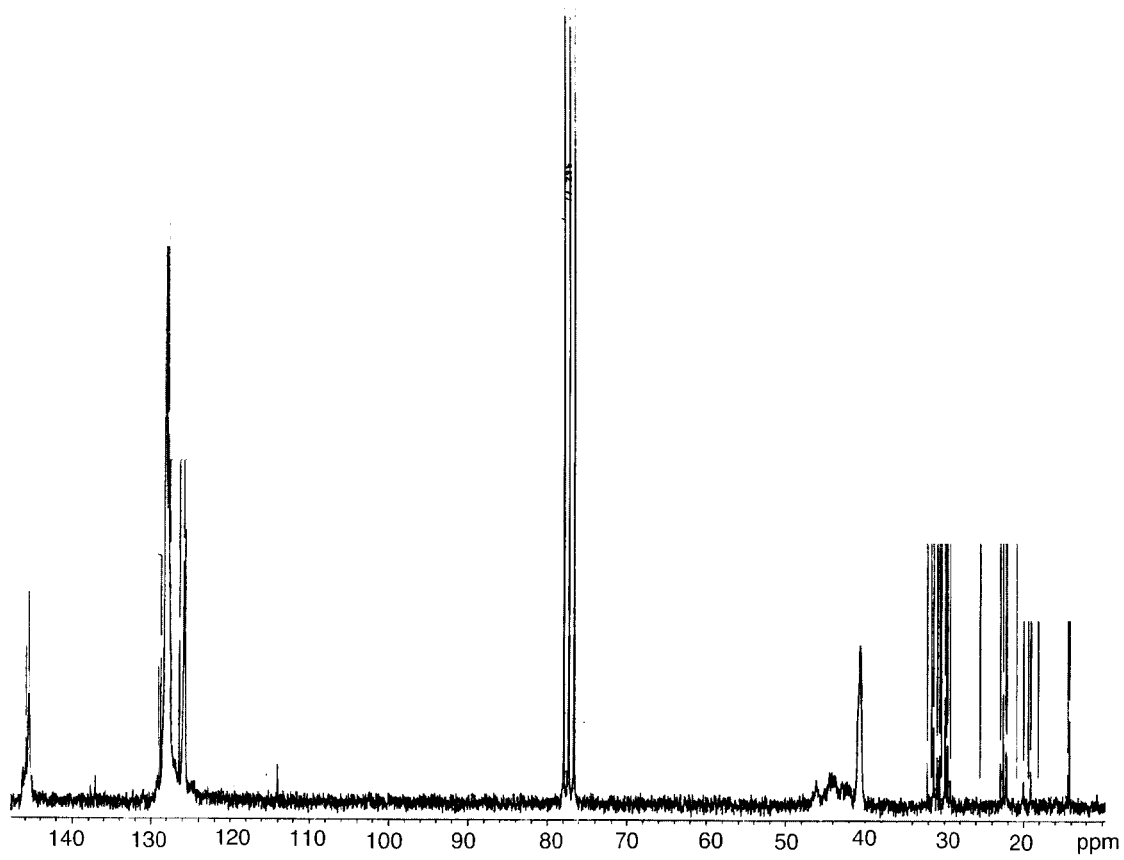
FIG. 16 is a $^{13}$C NMR spectrum of a polystyrene polymer (D2) produced in accordance with an embodiment of the present disclosure.
Figure 17:
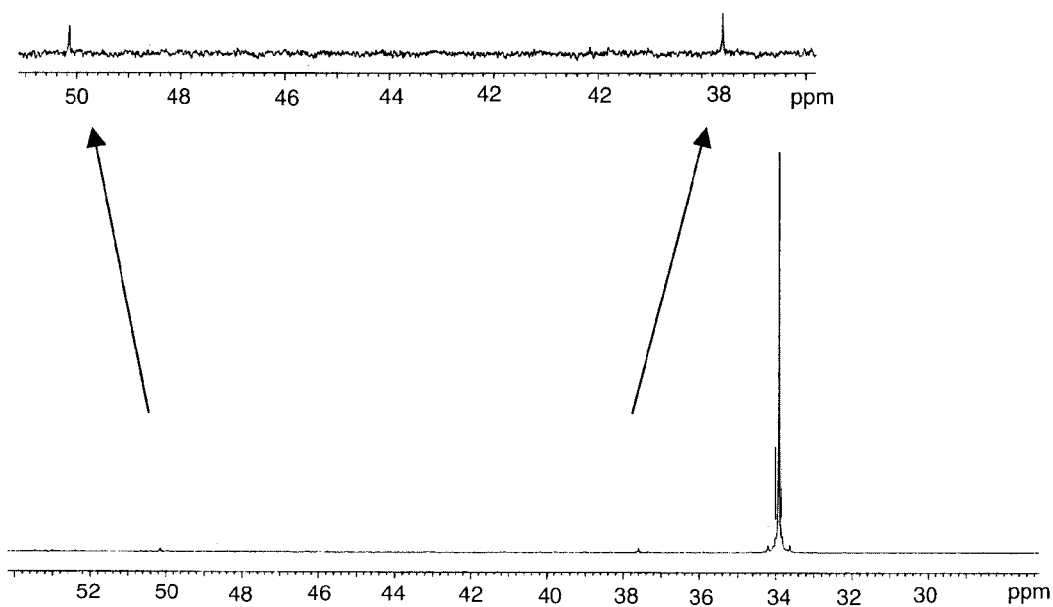
FIG. 17 is a $^{31}$P NMR spectrum of a polystyrene polymer (D2) produced in accordance with an embodiment of the present disclosure.

FIG. 15 shows the $^1$H NMR of the polymer D2, while FIG. 16 shows the $^{13}$C-NMR, and FIG. 17 shows the $^{31}$P-NMR. It is clear from these FIGS. 15-17 that there are three environments for phosphorous, one comparable to a free cation while the other two are down field, which means they are at lower electron density environments, as these two environments are much less populated.

Example 5

Preparation of Polystyrene (Polymer E3) from Decanted Liquid

Figure 18:
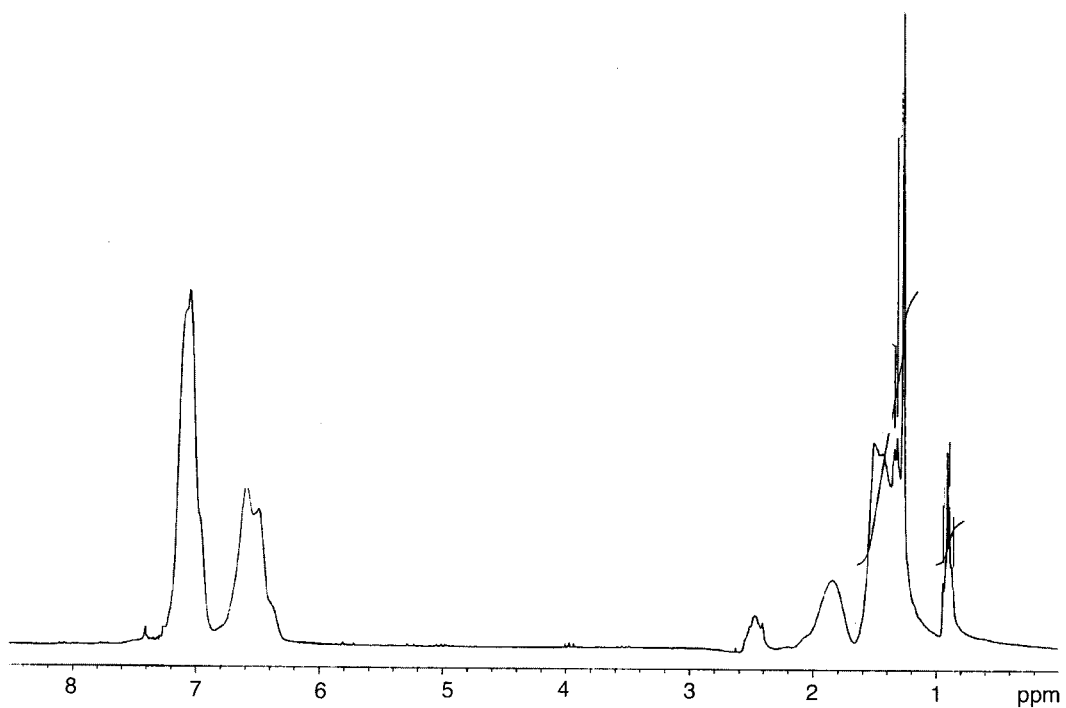
FIG. 18 is an $^1$H NMR spectrum of a polystyrene polymer (E3) produced in accordance with an embodiment of the present disclosure.
Figure 19:
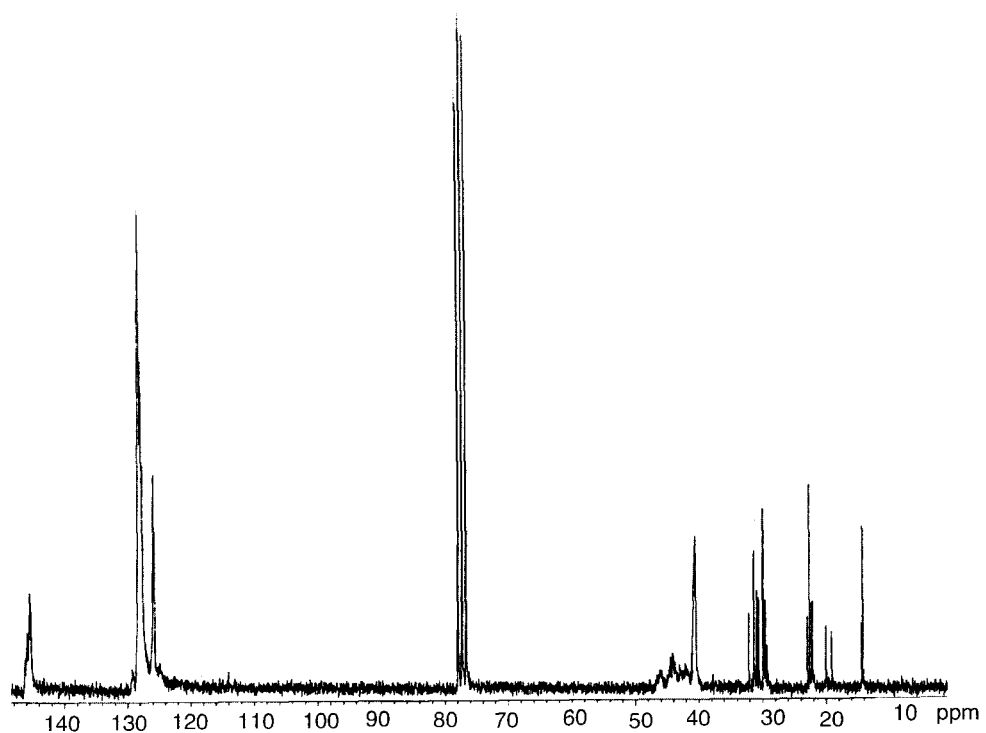
FIG. 19 is a $^{13}$C NMR spectrum of a polystyrene polymer (E3) produced in accordance with an embodiment of the present disclosure.
Figure 20:
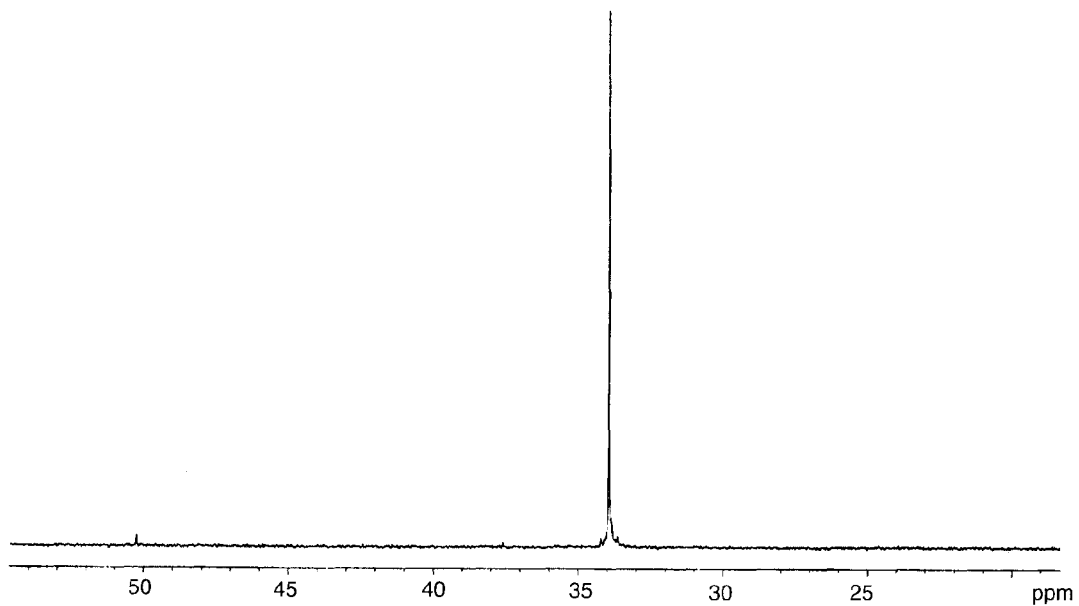
FIG. 20 is a $^{31}$P NMR spectrum of a polystyrene polymer (E3) produced in accordance with an embodiment of the present disclosure.

The decanted liquid from Example 4 (a homogenous, white, opaque liquid) was heated to 80° C. and the white homogenous solution rapidly segregated into a separate ionic liquid layer and clear polymer layer (which was on top). After 10 minutes, as the temperature approached 100° C., bubbles formed as water evaporated. The polymer began to harden and become a malleable conglomerate that stuck to the side of the glassware after stirring took place (which was necessary to facilitate the evolution of all of the water). After 10 minutes, as the temperature approached 120° C., the bubbles continued to evolve at a fast rate. After 1 hour at this temperature, the polymer sample was removed from the vial, washed with methanol and suction filtrated with additional washings of methanol. Isolated yield was 0.7659 g of hard polymer. The NMR spectra of the polymer in CDCl$_3$ are presented in FIGS. 18-20 ($^1$H-NMR $^{13}$C-NMR and $^{31}$P-NMR).

Example 6

Preparation of Polystyrene (Polymers C1 and C2) in IL-104

1.9047 g of IL-104® (trihexyl(tetradecyl)phosphonium bis-2,4,4-(trimethylpentyl)phosphinate) and 2.2390 g styrene were combined in a 20 mL beaker. The mixture was put into an oil bath at 123° C. 0.12 g H$_2$O$_2$ was then added. After 5 minutes, the mixture became more opaque which suggests large molecular weight polymers had formed. This sample was then divided into two halves, C1 and C2.

For the polymer C1, 1.2121 g of water was added to the mixture. The mixture was then placed into an oil bath at 120° C. with stirring for 25 minutes, resulting in a now hard, with a mass of 0.922 g.

For the polymer C2, the sample was washed with MeOH. After 16 minutes at 120° C. with stirring, polymer C2 was had been washed of MeOH, resulting in a hard particles of polymer with a mass of 0.6834 g. The total yield of C1 and C2 is about 40%.

Example 7

Preparation of Polystyrene (Polymer C3) in IL-105®

1.7726 g of IL-105 (trihexyl(tetradecyl)phosphonium dicyanamide and 2.3552 g styrene were combined in a 20 mL beaker. The mixture was placed into an oil bath at 123° C., at which point 0.12 g of $H_2O_2$ was added. After 120 minutes, the polymer formed at the bottom. The sample was washed with methanol, resulting in polymer C3, which had a golden colour. The liquid on top of the polymer was decanted and allowed to settle, resulting in a white styrene polymer.

Example 8

Figure 21:
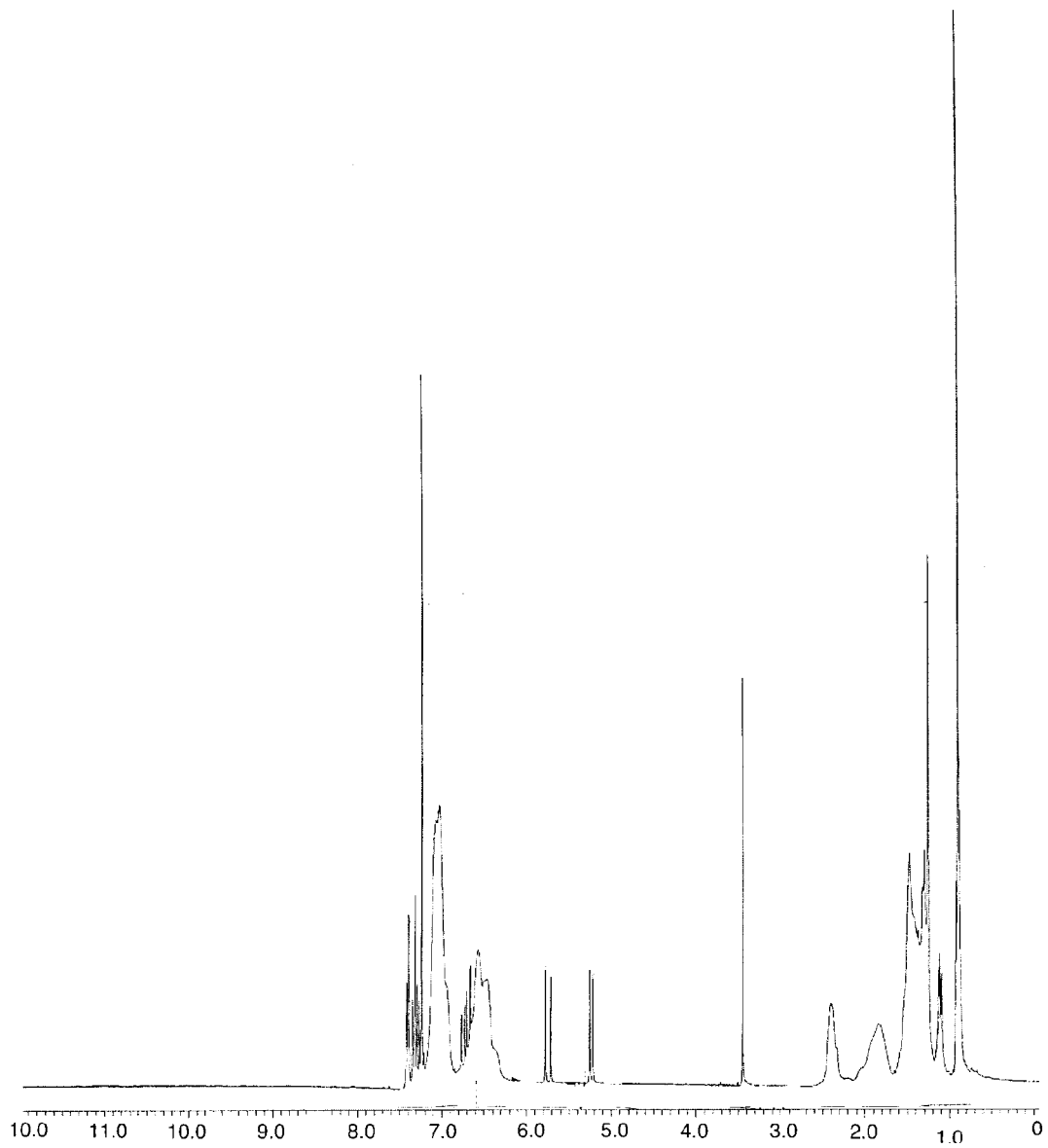
FIG. 21 is an $^1$H NMR spectrum of a polystyrene polymer (C2) produced in accordance with an embodiment of the present disclosure.
Figure 22:
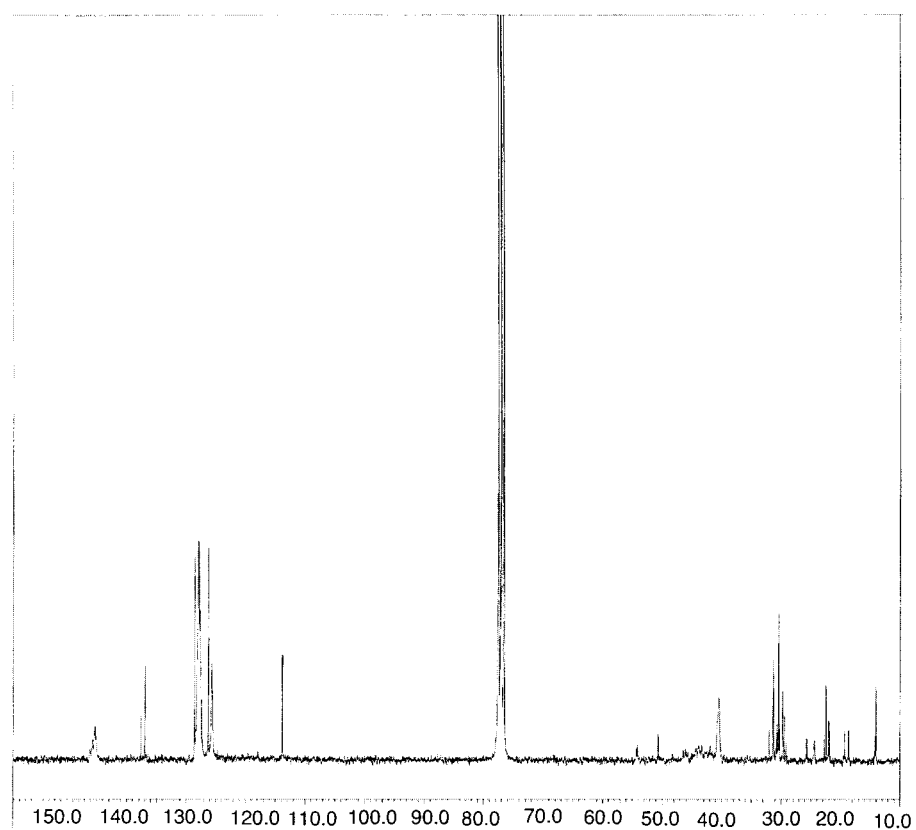
FIG. 22 is a $^{13}$C NMR spectrum of a polystyrene polymer (C2) produced in accordance with an embodiment of the present disclosure.
Figure 23:
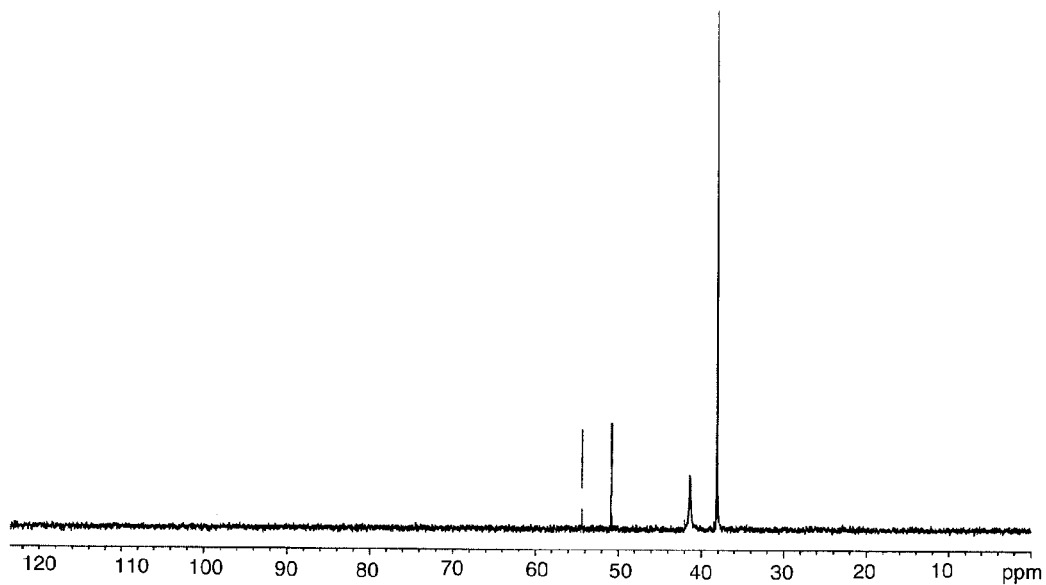
FIG. 23 is a $^{31}$P NMR spectrum of a polystyrene polymer (C2) produced in accordance with an embodiment of the present disclosure.

Preparation of Polystyrene (Polymer C2) in IL-104 Using Microwave Energy 1.9047 g of IL-104® (trihexyl(tetradecyl)phosphonium bis-2,4,4-(trimethylpentyl)phosphinate) and 2.2390 g styrene were combined in a 20 mL beaker. 0.12 g $H_2O_2$ was then added and the mixture exposed to microwave radiation, which resulted in the polymer C2 after 60 minutes. The NMR spectra of the polymer is shown in FIGS. 21-23.

Discussion

The NMR spectrums (FIG. 21-23) of polymer C2 suggests atactic polystyrene with phosphonium cations as well as anions in between aromatic ring.

Example 9

Preparation of Magnetic Polystyrene (Polymer M1)

2 mL of IL-101 and 2.2390 of g styrene were combined in a 20 mL beaker. 0.5 mL of $H_2O_2$ was then added, along with 0.4764 g of copper chloride ($CuCl_2$). The solution was then exposed to microwave radiation for 60 minutes, which resulted in a soft polymer possessing magnetic properties.

Figure 24:
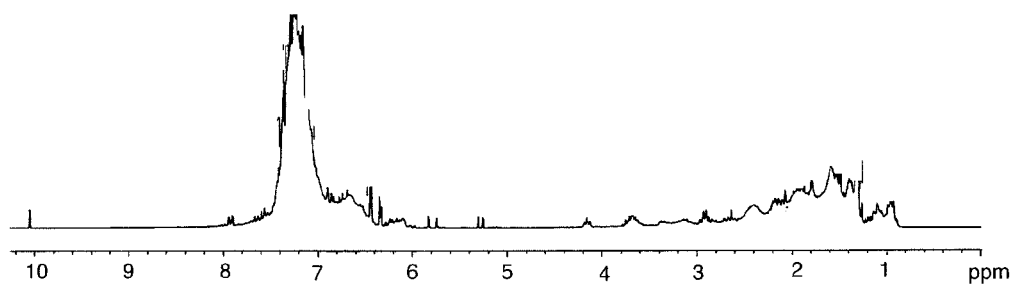
FIG. 24 is an $^1$H NMR spectrum of a polystyrene polymer (M1) produced in accordance with an embodiment of the present disclosure.
Figure 25:
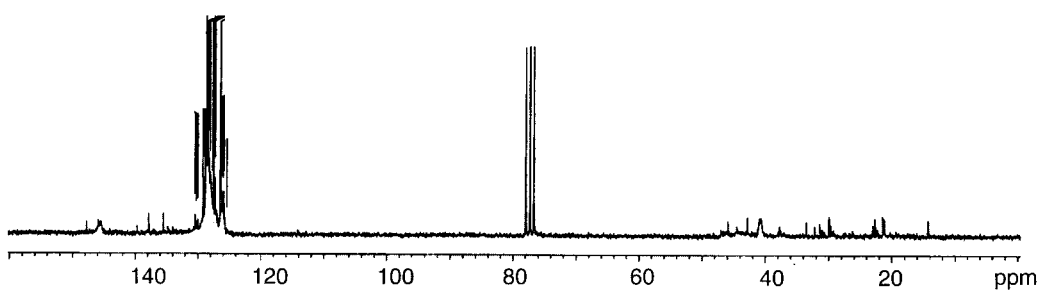
FIG. 25 is a $^{13}$C NMR spectrum of a polystyrene polymer (M1) produced in accordance with an embodiment of the present disclosure.
Figure 26:
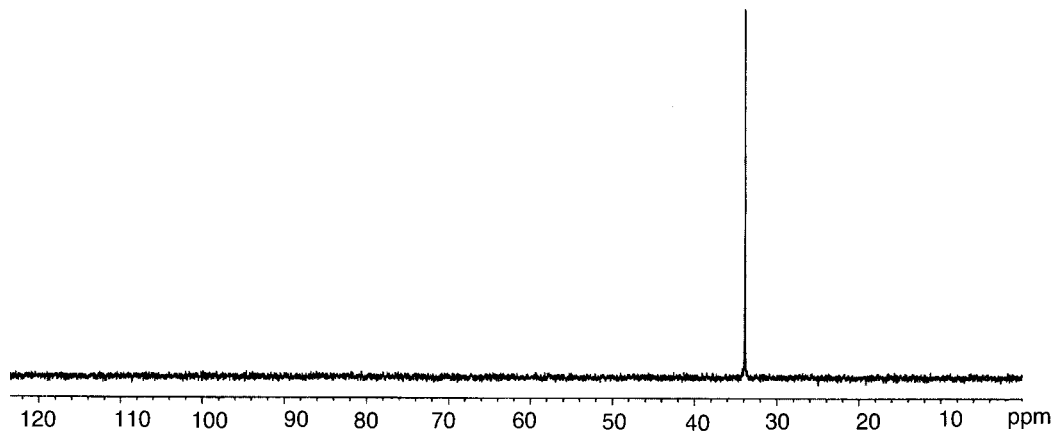
FIG. 26 is a $^{31}$P NMR spectrum of a polystyrene polymer (M1) produced in accordance with an embodiment of the present disclosure.

FIGS. 24-26 show the NMR spectra (proton, carbon, and phosphorous NMR respectively) of this polymer (Polymer M1).

Example 10

Preparation of Gold-Polystyrene Composite (Polymer G1)

5 mg $HAuCl_4.3H_2O$ was combined with 95 mL deionized $H_2O$ and heated to 100° C. Once the solution reached 100° C., 5 mL of sodium citrate was added and heated at this temperature for 30 minutes.

In a separate beaker, 2.03 mL of IL-101, 2 mL of styrene, 2 mL of the gold nanoparticles from the water solution (~50 nm) and 0.5 mL of $H_2O$ were mixed together. The mixture was heated in a microwave at 90° C. for one hour.

Figure 27:
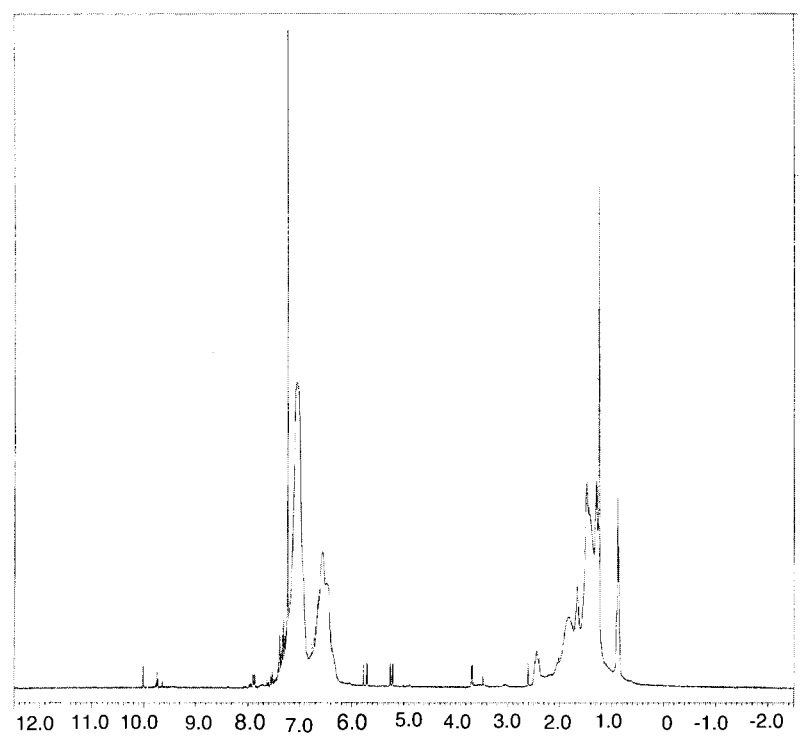
FIG. 27 is a $^1$H NMR spectrum of a polystyrene polymer (G1) produced in accordance with an embodiment of the present disclosure.
Figure 28:
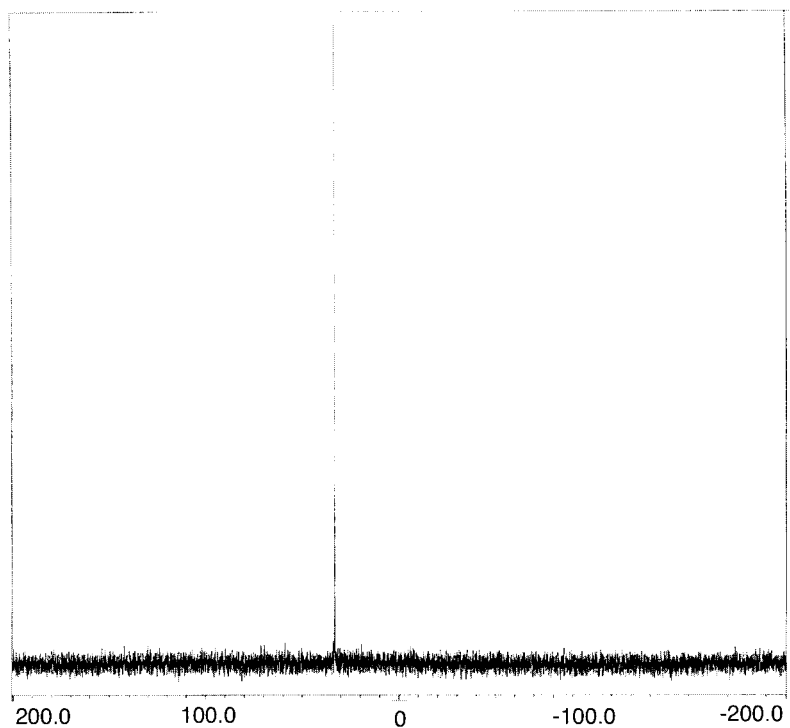
FIG. 28 is a $^{31}$P-NMR spectrum of a polystyrene polymer (G1) produced in accordance with an embodiment of the present disclosure.

FIG. 27 shows a $^1H$ NMR spectrum of the gold-composite polymer G1, while FIG. 28 shows a $^{31}P$-NMR spectrum.

Example 11

Preparation of Polystyrene (Polymer A4)

A 10 mL Erlenmeyer flask was first charged with 1.7771 g of IL-101, to which 2.00 mL styrene and 50 μL ml $H_2O_2$ (via pipette) was added. The Erlenmeyer was heated in an oil bath to 124° C. over night. The total mixture turned into a solid polymer. Accordingly, the yield was 100%.

Discussion

Figure 29:
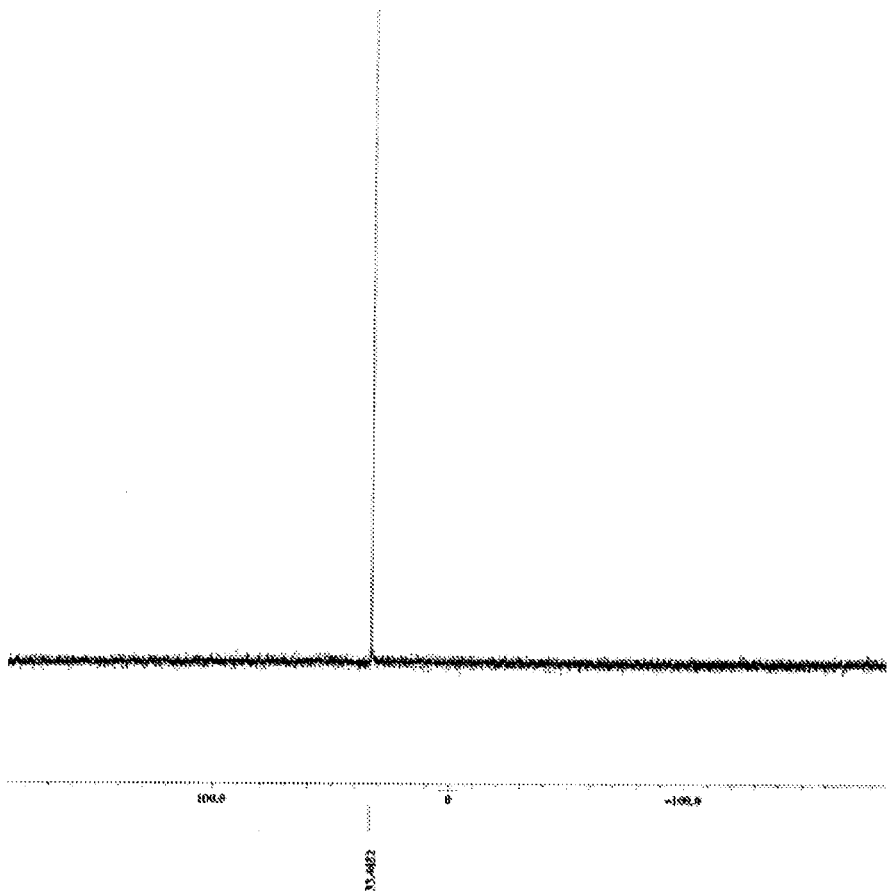
FIG. 29 is a $^{31}$P-NMR spectrum of a polystyrene polymer (A4) produced in accordance with an embodiment of the present disclosure.

The $^{31}P$-NMR spectrum of the polymer (A4) is shown in FIG. 29, in which there is only one chemical environment for the phosphorous atom.

FULL CITATIONS FOR DOCUMENTS REFERRED TO IN THE SPECIFICATION

1) J. Ryan et al., Macromol. Rapid Commun, 2004, 25, 930.
2) R. Sheldon, Chem. Commun. 2001, 2399.
3) K. Hong, et al., Chem. Commun. 2002, 1368.
4) S. Harrison, Macromolecules 2003, 36, 5072.
5) A. J. Carmichael, et al., Chem. Commun. 2000, 1237.
6) T. Biedron, P. Kubisa, Macromol. Rapid Commun. 2001, 22, 1237.
7) T. Sarbu, K. Matyjaszewski, Macromol. Chem. Phys. 2001, 202, 3379.
8) P. Cormier, et al., J. Phys. Chem. A, 2008, 112, 4593.
9) P. Cormier, et al., Physica B, 2009, 404, 930.
10) K. Ghandi, et al., Phys. Chem. Chem. Phys., 2007, 9, 353.
11) J. M. Lauzon, et al., Phys. Chem. Chem. Phys., 2008, 10, 5957.
12) B. A. Taylor, et al., Physica B, 2009, 404, 936.
13) N. Ishihara et al. *Macromolecules* 1986, 19, 2464.

The invention claimed is:

1. A polymer composite comprising a polystyrene or a polystyrene derivative comprising styrene or styrene derivative monomer units in which at least about 1% (mole fraction) of a phosphonium ion salt ionic liquid is incorporated into the structure of the polystyrene or polystyrene derivative.

2. The polymer composite according to claim 1, wherein the styrene or styrene derivative monomer unit is a compound of the formula (I)

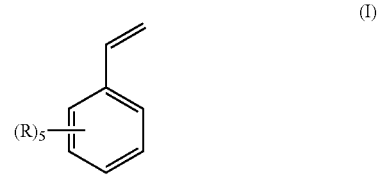

wherein each R is simultaneously or independently H, halo or $C_{1-4}$alkyl, the latter group being optionally substituted by halo, $C_{1-2}$alkyl or fluoro-substituted $C_{1-2}$alkyl.

3. The polymer composite according to claim 1, wherein the phosphonium ion salt has the structure:

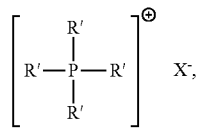

wherein
each $R^1$ is independently or simultaneously $C_{1-20}$alkyl and X is any suitable anionic ligand.

4. The polymer composite according to claim 3, wherein the phosphonium ion salt ionic liquid is selected from

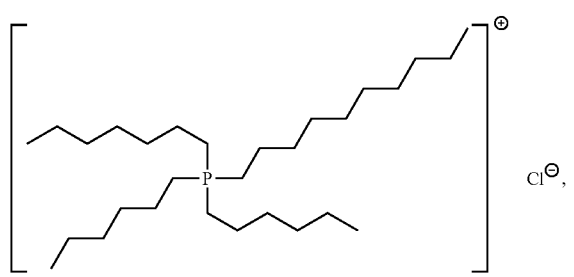

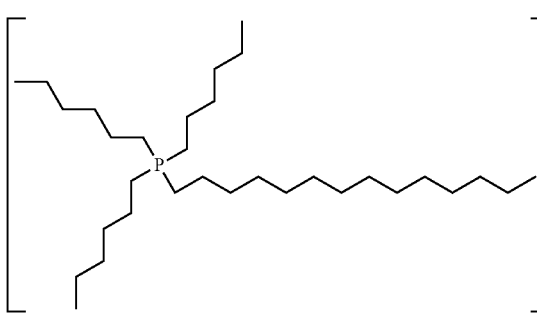

and

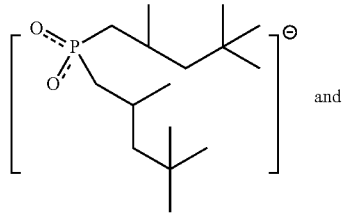

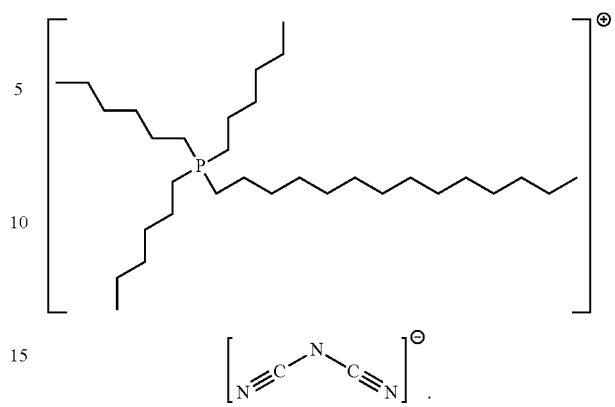

5. The polymer composite according to claim 1, wherein the polymer further comprises a metal dopant.

6. The polymer composite according to claim 5, wherein the metal dopant is magnetic.

7. The polymer composite according to claim 6, wherein the magnetic metal dopant comprises copper or gold.

8. A process for the production of polystyrene or a polystyrene derivative, comprising polymerizing styrene or styrene derivative monomer units in a phosphonium ion salt ionic liquid in the presence of a free radical initiator at a pressure of about 0.8 to about 1.2 atmospheres, under conditions for the polymerization of the styrene or styrene derivative monomer units, in which at least about 1% (mole fraction) of the phosphonium ion salt ionic liquid is incorporated into the structure of the polystyrene or polystyrene derivative.

9. The process according to claim 8, wherein the phosphonium ion salt ionic liquid has the structure:

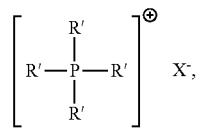

wherein
each R' is independently or simultaneously $C_{1-20}$alkyl and X is any suitable anionic ligand.

10. The process according to claim 9, wherein the phosphonium ion salt ionic liquid is selected from

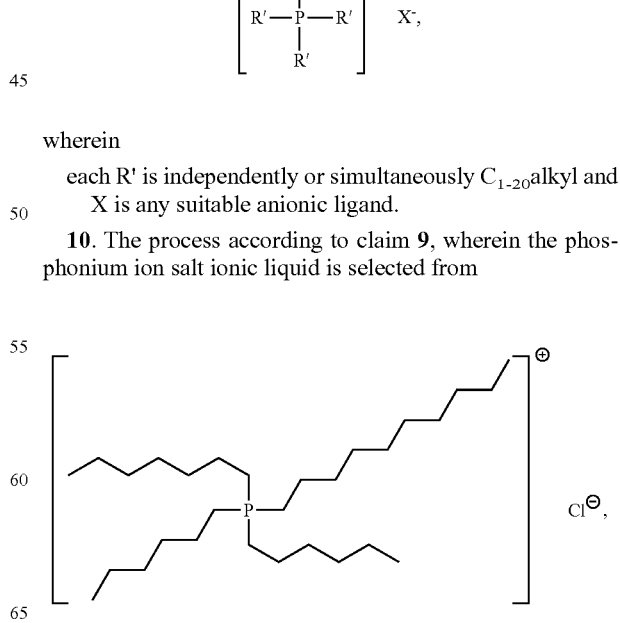

-continued

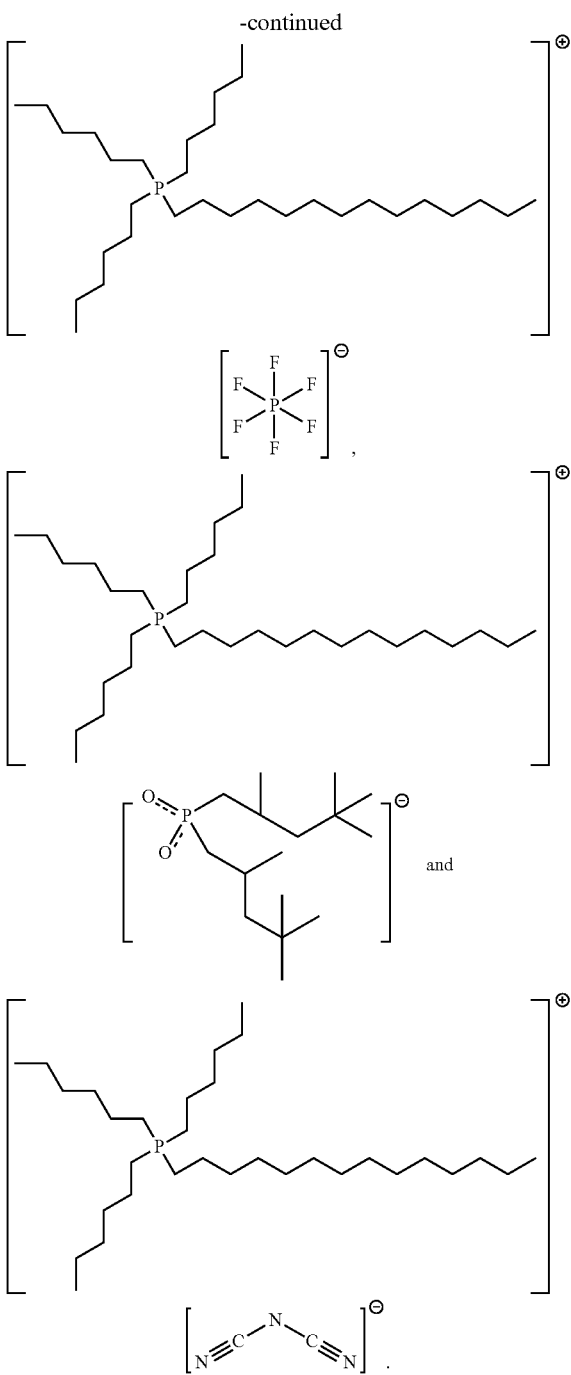

11. The process according to claim 8, wherein the styrene or styrene derivative monomer unit is a compound of the formula (I):

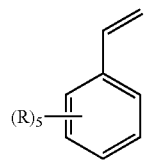

(I)

wherein
each R is simultaneously or independently H, halo or $C_{1-4}$alkyl, the latter group being optionally substituted by halo, $C_{1-2}$alkyl or fluoro-substituted $C_{1-2}$alkyl.

12. The process according to claim 8, wherein the free radical initiator is selected from benzoyl peroxide, hydrogen peroxide and azobisisobutyronitrile (AIBN).

13. The process according to claim 8, wherein the polymerization is performed at about atmospheric pressure.

14. The process according to claim 8, wherein the conditions for the polymerization of the styrene or styrene derivative monomer units comprise a mole fraction ratio of the styrene or styrene derivative monomer units to the phosphonium ion salt ionic liquid of about 0.10:1.0 to about 2.0:1.0 (styrene or styrene derivative monomer units:ionic liquid).

15. The process according to claim 8, wherein the conditions for the polymerization of the styrene or styrene derivative monomer units comprise microwave energy.

16. The process according to claim 8, wherein the conditions for the polymerization of the styrene or styrene derivative monomer units comprise ultraviolet light.

17. The process according to claim 8, wherein the process results in no waste products.

18. The process according to claim 8, wherein the process proceeds with 100% yield.

19. The process according to claim 8, wherein the polystyrene or a polystyrene derivative precipitates from the phosphonium ion salt ionic liquid leaving unreacted styrene or styrene derivative monomer units and ionic liquid, wherein the unreacted styrene or styrene derivative monomer units and ionic liquid are further reacted using the process of claim 8.

20. The process according to claim 19, wherein the yield of the polystyrene or polystyrene derivative is at least 90%.

* * * * *